(12) United States Patent
Shichi et al.

(10) Patent No.: US 7,709,062 B2
(45) Date of Patent: May 4, 2010

(54) REFILLING METHOD BY ION BEAM, INSTRUMENT FOR FABRICATION AND OBSERVATION BY ION BEAM, AND MANUFACTURING METHOD OF ELECTRONIC DEVICE

(75) Inventors: Hiroyasu Shichi, Tokyo (JP); Muneyuki Fukuda, Kokubunji (JP); Isamu Sekihara, Fussa (JP); Satoshi Tomimatsu, Kokubunji (JP); Kaoru Umemura, Musashino (JP)

(73) Assignee: Hitachi High-Technologies Corporation, Tokyo (JP)

( * ) Notice: Subject to any disclaimer, the term of this patent is extended or adjusted under 35 U.S.C. 154(b) by 292 days.

(21) Appl. No.: 10/322,591

(22) Filed: Dec. 19, 2002

(65) Prior Publication Data

US 2003/0198755 A1    Oct. 23, 2003

(30) Foreign Application Priority Data

Apr. 22, 2002    (JP)    ............................. 2002-118797

(51) Int. Cl.
C23C 14/46    (2006.01)
C23C 16/48    (2006.01)
B05D 5/00    (2006.01)
B05D 1/26    (2006.01)

(52) U.S. Cl. ........................ 427/524; 427/526; 427/595; 204/192.11

(58) Field of Classification Search ...................... 427/8, 427/9, 10, 523, 526, 527, 529, 530, 533, 427/552, 595

See application file for complete search history.

(56) References Cited

U.S. PATENT DOCUMENTS

| | | | | |
|---|---|---|---|---|
| 4,548,883 A | * | 10/1985 | Wagner | 430/5 |
| 4,639,301 A | * | 1/1987 | Doherty et al. | 250/251 |
| 4,868,068 A | * | 9/1989 | Yamaguchi et al. | 428/596 |
| 4,874,493 A | * | 10/1989 | Pan | 204/192.11 |
| 4,902,530 A | * | 2/1990 | Yasaka et al. | 427/526 |
| 4,915,806 A | * | 4/1990 | Lardon et al. | 427/524 |
| 4,936,968 A | * | 6/1990 | Ohnishi et al. | 204/192.34 |
| 5,026,664 A | * | 6/1991 | Hongo et al. | 438/625 |
| 5,104,684 A | * | 4/1992 | Tao et al. | 427/526 |
| 5,113,072 A | * | 5/1992 | Yamaguchi et al. | 250/309 |
| 5,140,164 A | * | 8/1992 | Talbot et al. | 250/492.2 |

(Continued)

FOREIGN PATENT DOCUMENTS

| | | | | |
|---|---|---|---|---|
| JP | 01-234564 | * | 9/1989 | ............ 204/192.11 |
| JP | 02-152155 A | * | 6/1990 | ................. 250/311 |

(Continued)

*Primary Examiner*—Marianne L Padgett
(74) *Attorney, Agent, or Firm*—Mattingly & Malur, P.C.

(57) ABSTRACT

A hole in a sample from which a sample piece has been extracted with a focused ion beam is filled at high speed using ion beam gas assisted deposition. A method of filling the hole by using the ion beam includes a step of irradiating the hole formed in a face of the sample with the ion beam to thereby form an ion beam gas-assisted deposition layer in the hole. The ion beam gas-assisted deposition layer is formed in the hole while controlling the area to which the ion beam is irradiated so as to cause the ion beam to fall on a part of a side wall of the hole and to not fall on another part of the side wall in an area scanned with the ion beam. The filled hole may then be covered with a protective film.

13 Claims, 13 Drawing Sheets

U.S. PATENT DOCUMENTS

| | | | |
|---|---|---|---|
| 5,270,552 A | 12/1993 | Ohnishi et al. | |
| 5,504,340 A * | 4/1996 | Mizumura et al. | 250/492.21 |
| 5,591,970 A * | 1/1997 | Komano et al. | 250/309 |
| 5,639,699 A * | 6/1997 | Nakamura et al. | 427/527 |
| 5,700,526 A * | 12/1997 | Ximen et al. | 427/527 |
| 5,844,416 A * | 12/1998 | Campbell et al. | 324/750 |
| 6,106,677 A * | 8/2000 | Sandhu | 204/192.3 |
| 6,322,935 B1 * | 11/2001 | Smith | 430/5 |
| 6,331,712 B1 * | 12/2001 | Sugiyama et al. | 250/492.21 |
| 6,670,717 B2 * | 12/2003 | Kane et al. | 257/774 |
| 6,703,626 B2 * | 3/2004 | Takaoka et al. | 250/492.21 |
| 6,740,368 B2 * | 5/2004 | Kaito | 427/586 |
| 6,828,566 B2 * | 12/2004 | Tomimatsu et al. | 250/442.11 |
| 6,858,851 B2 * | 2/2005 | Tomimatsu et al. | 250/442.11 |
| 6,891,171 B1 * | 5/2005 | Hagiwara et al. | 430/5 |
| 7,132,673 B2 * | 11/2006 | Fischione et al. | 250/492.3 |
| 7,205,560 B2 * | 4/2007 | Tokuda et al. | 250/492.3 |
| 7,268,356 B2 * | 9/2007 | Shichi et al. | 250/492.21 |
| 7,315,023 B2 * | 1/2008 | Moore | 250/311 |
| 7,372,050 B2 * | 5/2008 | Fukuda et al. | 250/492.21 |
| 2003/0161970 A1 * | 8/2003 | Kaito | 427/595 |
| 2004/0121069 A1 * | 6/2004 | Ferranti et al. | 427/140 |
| 2006/0284112 A1 * | 12/2006 | Tomimatsu et al. | 250/492.1 |
| 2006/0284115 A1 * | 12/2006 | Kaneoka et al. | 250/492.21 |
| 2007/0114460 A1 * | 5/2007 | Muramatsu et al. | 250/492.22 |
| 2007/0158560 A1 * | 7/2007 | Kaneoka et al. | 250/309 |
| 2008/0073582 A1 * | 3/2008 | Shichi et al. | 250/492.21 |
| 2008/0073586 A1 * | 3/2008 | Iwasaki | 250/492.21 |
| 2008/0302979 A1 * | 12/2008 | Kozakai | 250/492.21 |

FOREIGN PATENT DOCUMENTS

| | | | | |
|---|---|---|---|---|
| JP | 4-56240 | * | 2/1992 | 438/17 |
| JP | 5-52721 | | 3/1993 | |
| JP | 06-252233 | | 9/1994 | |
| JP | 6-260129 | | 9/1994 | |
| JP | 10-116872 | | 5/1998 | |
| JP | 2000-156393 | | 6/2000 | |
| JP | 2002-139827 A | * | 5/2002 | |
| WO | WO 99/17103 | | 4/1999 | |

* cited by examiner

STAGE TILT

GROWING DIRECTION

REFILLING METHOD BY ION BEAM, INSTRUMENT FOR FABRICATION AND OBSERVATION BY ION BEAM, AND MANUFACTURING METHOD OF ELECTRONIC DEVICE

BACKGROUND OF THE INVENTION

The present invention relates to a technique of inspecting an electronic device and, more particularly, to a technique of fabricating and observing an electronic device, such as a semiconductor device, by using an ion beam.

In fabrication of electronic devices, such as a semiconductor memory (typified by a dynamic random access memory (DRAM)), a microprocessor, a semiconductor device, such as a semiconductor laser, and a magnetic head, manufacture at a high yield is demanded.

Reduction in the product yield due to occurrence of a defect causes deterioration in profitability. Consequently, it is a big task to discover a failure, a foreign matter, and poor processing as causes of a defect early and to take an early countermeasure. For example, at a manufacturing site of a semiconductor device, energies are put into early defect discovery by a careful inspection and analysis of the cause of the defect. In a process of fabricating actual electronic devices using a substrate, a completed substrate is inspected, the cause of an abnormal part, such as a defect in a circuit pattern or a foreign matter, is pursued, and a countermeasure is examined.

Usually, a high-resolution scanning electron microscope (hereinbelow, abbreviated as SEM) is used for observing a detailed structure of a sample. As the packing density of a semiconductor increases, it is becoming impossible to observe an object using the resolution of the SEM, and a transmission electron microscope (hereinbelow, abbreviated as TEM) having a higher observation resolution is used in place of the SEM.

Fabrication of a conventional sample for a TEM includes extracting a small piece from a sample by cleavage, cutting, or the like. In the case where a sample is a substrate, in most cases, the substrate has to be cut.

Recently, there is an example of using a processing method of irradiating a sample with an ion beam so that particles making up the sample are discharged from the sample by a sputtering action, that is, using a focused ion beam (hereinbelow, abbreviated as FIB) process.

According to the method, first, a rectangular-shaped pellet in the sub-millimeter range, including an area to be observed, is cut out from a sample, such as a substrate, by using a dicer, or the like. Subsequently, a part of the rectangular-shaped pellet is processed with an FIB so as to thin-out the film, thereby obtaining a TEM sample. The feature of the FIB-processed sample for TEM observation is that a part of the sample is thinned-out to a thin film having a thickness of about 100 nm so as to be able to be observed using the TEM. Although the method enables a desired observation part to be positioned with precision of a micrometer level and observed, the substrate still has to be cut.

As described above, although the advantage of monitoring a result of a process during fabrication of a semiconductor device or the like is big from the viewpoint of yield management, the substrate is cut in the fabrication of the sample as described above, and the piece of the substrate is not subjected to the following process, but is instead discarded. Particularly, in recent years, the diameter of wafers has increased in order to lower the unit price of fabricating a semiconductor device. To be specific, the number of semiconductor devices which can be fabricated from one wafer has increased, thereby reducing the unit price. However, the price of each wafer has increased, and the number of semiconductor devices which are lost by discarding a wafer has also increased. Therefore, the conventional inspection method that includes cutting of a wafer is very uneconomical.

Addressing this problem, there is a method capable of obtaining a sample without cutting a wafer. The method is disclosed in Japanese Patent Application Laid-Open No. 05-52721. According to the method, as shown in FIG. 2A, the posture of a sample 2 is kept so that the surface of the sample 2 is irradiated with an FIB 1 at a right angle, and a rectangular area in the surface of the sample 2 is scanned with the FIB 1, thereby forming a rectangular hole 101 having a required depth in the surface of the sample 2. As shown in FIG. 2B, the sample 2 is tilted and a bottom hole 102 is formed. The tilt angle of the sample 2 is changed by a specimen stage (not shown). Subsequently, the posture of the sample 2 is changed and, as shown in FIG. 2C, the sample 2 is set so that the surface of the sample 2 becomes perpendicular to the FIB 1 again, and a trench 103 is formed. A manipulator (not shown) is driven to make the tip of a probe 3 at the end of the manipulator come into contact with a part to be separated in the sample 2, as shown in FIG. 2D.

As shown in FIG. 2E, while supplying a deposition gas 5 from a nozzle 104 for delivering gas, an area including the tip portion of the probe 3 is locally irradiated with the FIB 1, thereby forming an ion beam gas assisted deposition layer (hereinbelow, simply called deposition layer 4). The separation part in the sample 2 and the tip of the probe 3 which are in contact with each other are connected by the deposition layer 4. As shown in FIG. 2F, the remaining part is cut with the FIB 1 and a micro sample 6 as a separate sample is cut out from the sample 2. The cut-out separate sample 6 is supported by the probe 3 connected as shown in FIG. 2G. The micro sample 6 is processed with the FIB 1 and an area to be observed is wall-processed, thereby obtaining a TEM sample (not shown).

As described above, the method is a method of separating a micro sample including a desired area to be analyzed from a sample, such as a wafer, by using the FIB process and means of carrying the micro sample. By introducing the micro sample separated by the method into various analyzers, analysis can be made.

The method of cutting out a micro sample for inspection from a sample without cutting a wafer and allowing the wafer to be continuously subjected to the following process is disclosed in Japanese Patent Application Laid-Open No. 2000-156393. According to this method, there is no semiconductor device which is lost when a wafer is cut, so that total fabrication cost of semiconductor devices can be reduced.

In fabrication of electronic devices as described above, in the case of allowing the wafer to be subjected to the next process, a process for forming hole from which the micro sample is taken out is necessary. In other words, when the formed hole is not processed, the following problems occur.

(1) An end of the hole is broken off and becomes a contamination source. (2) The hole causes an uneven shape of the wafer at the time of spin coating, polishing, or the like. (3) Dusts gather in the hole. For example, in the case of performing CMP (Chemical & Mechanical Polishing) after taking out a micro sample, CMP grains enter the hole and all of these grains cannot be taken away by cleaning. In any processes after performing CMP, a CMP grain can come out of the hole and become foreign matter or cause impurity contamination, which fluctuates device characteristics.

A method related to the technique of putting a wafer subjected to an FIB process back into a process line is disclosed in Japanese Patent Application Laid-Open No. 6-260129. According to this method, in order to put a sample irradiated with a focused ion beam using gallium as an ion source back into a process, either a part to which gallium has been implanted is removed by using an ion beam of a gaseous element which does not exert a conspicuous influence on the characteristics of a sample, or an organic metal film is deposited using an energy beam so as to cover a portion in which gallium is implanted. Specifically, an area to be processed and observed is cleaned by using any of argon, oxygen ions, and oxygen radicals, a compound is deposited and, after that, the sample is put back into the fabrication process.

In an instrument of the method, however, Ga contamination is considered, but a process for addressing an opened hole is not considered.

A method related to the technique of putting a wafer back into a process line after a cross section inspection is disclosed in Japanese Patent Application Laid-Open No. 10-116872. In the disclosed method, a cross section of a wafer is inspected during a semiconductor device process. A hole opened for obtaining the section is filled with an insulator or a conductive film by energy-beam-induced CVD (Chemical Vapor Deposition, although a technical term of CVD is conventionally used, gas-assisted deposition is used as a synonym), or is filled with a desired film by applying a liquid material and irradiating the material with an energy beam. The wafer is put back to a fabrication process line, and the fabrication is continued. Particularly, it is disclosed that a wafer is taken out, a cross section inspection is performed, and the inspected part in the wafer is planarized with an ion beam.

International Publication Number WO 99/17103 discloses a method of covering a hole opened with an FIB with a dielectric by using an ion beam.

However, the conventional hole filling method after the FIB process has the following problems.

First, in the case of filling a hole by the energy-beam-induced gas-assisted deposition, the following problems occur depending on the kinds of beams.

(1) In the case of forming a film by applying a liquid material and irradiating the material with an energy beam, when a film is thick, a crack occurs in the film in a process of irradiating the material with the energy beam. If the wafer is subjected to the following process, it is feared that a piece from the crack can disperse and cause a defect. The depth of an opened hole from which a micro sample is taken out is generally at least 3 to 5 micrometers. On the other hand, the thickness of a film which can be formed without a crack from an oxide film material which is generally used as the liquid material is at most 1 to 2 micrometers. A crack can occur during a heating process in an oxide film applied thicker than that. (2) In laser-beam-induced gas-assisted deposition, a film grows isotropically, so that it is difficult to fill a hole so that the surface is flat. (3) In argon ion beam induced gas-assisted deposition, the beam size in an inexpensive ion emitting system is generally 50 to 500 micrometers. On the other hand, the size of a hole is at most 20 micrometers. It is therefore difficult to form a film only in the hole, but instead a film is formed not only in the hole but also over the periphery of the hole. Thus, it is difficult to fill the hole while realizing a flat surface. (4) In electronic beam induced gas-assisted deposition, deposition speed is generally low and it is difficult to fill the hole within practical time such as within 10 minutes.

(5) In gallium FIB induced gas assisted deposition, a deposition layer can be formed in the hole, but there is a problem such that gallium is taken into the deposition layer. Further, by a sputtering action by FIB irradiation, pieces of gallium and a sample are spread also to areas other than the FIB processed area. The possibility of the gallium contamination causing defects in the fabrication of semiconductor devices is high. Specifically, when nothing is done to address the contamination, and the wafer is subjected to the following process, gallium is diffused and enters a semiconductor device when subjected to the fabrication process, and problems such as poor electric characteristics and poor contacts occur. From the viewpoint of filling a hole at high speed, although the speed is faster as compared with the electron beam induced gas-assisted deposition, it is still difficult to fill the hole within a practical time, such as 10 minutes. Since the absolute amount of a deposition layer can be increased in proportion to an FIB current, then in order to increase the speed of filling a hole, the FIB current is increased. However, when the FIB current is increased to a high current of about 1 nA or higher, the deposition layer forming efficiency deteriorates. The deposition amount and the sputtering amount become almost equal to each other, so that growth of the deposition layer is stopped and a hole cannot be filled at high speed.

Consequently, for improvement in the yield of a semiconductor device and the like, to conduct an inspection during a process without cutting a wafer, the following techniques are demanded, such as a technique of filling at high speed a hole from which a micro sample has been taken out or a hole opened for inspecting a section, while achieving surface flatness. It is also demanded to establish a hole filling method by which a foreign matter is not generated and gallium contamination does not cause a defect in a semiconductor device, so that a problem does not occur in the subsequent processes, and to develop an apparatus capable of realizing the method.

Particularly, from the viewpoint of putting an inspected wafer back into a fabrication line, it is important to shorten the time required to inspect the wafer and put the wafer back into the fabrication line. In other words, a technique for increasing the speed of filling a hole is demanded, and the conventional methods do not address this demand. For example, a technique is desired that is capable of filling a hole at high speed with an increased deposition amount, and without deteriorating a deposition layer forming efficiency, even when the FIB current is increased, specifically, to a high current of about 1 nA or higher.

SUMMARY OF THE INVENTION

In consideration of these problems, an object of the present invention is to provide a technique of filling, at high speed with an FIB, a hole from which a sample has been taken out, and to provide a novel inspection and analysis method, an electronic device manufacturing method, and an instrument for fabrication and observation in which a wafer used for evaluation is not discarded uselessly and, even when a wafer from which a sample for inspection has been taken out is put back into a process, a defect does not occur.

The object is achieved in the following manner in the present invention.

(1) A method of filling a hole in a sample surface is disclosed by forming an ion beam gas-assisted deposition layer in the hole by a charged particle beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the charged particle gas-assisted deposition layer is formed in the hole while controlling the ion beam so as to fall on a part of a side wall of the hole and so as not to fall on another part of the side wall in an area scanned with the charged particles.

According to the method, a method is provided for filling, at high speed, a hole from which a sample has been extracted with an FIB.

(2) A method of filling a hole in a sample surface is disclosed by forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed by setting an area scanned with the ion beam to be almost the same as an opening area of the hole and controlling the scanning area so as to move with respect to the position of the hole.

According to the method, a method is provided for filling, at high speed, a hole from which a sample has been extracted with an FIB and, particularly, a method of filling a hole is provided in which setting of an ion beam scanning area is easy.

(3) A method of filling a hole in a sample surface is provided by forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed while controlling the ion beam so that the area scanned with the ion beam is moved so as to be apart from at least a part of the side wall of the hole.

According to the method, a method is provided for filling, at high speed, a hole from which a sample has been extracted with an FIB.

(4) A method is disclosed for filling a hole in a sample surface by forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole while controlling the ion beam so that a part of a side wall of the hole is irradiated with the ion beam and another part is not irradiated in an area scanned with the ion beam and controlling the ion beam so as to continuously reduce the area scanned with lapse of time of filling the hole.

According to the method, a method is provided for filling, at high speed, a hole from which a sample has been extracted with an FIB. Particularly, since the ion beam does not fall on areas other than the hole, a hole filling method for achieving a flat surface is provided.

(5) A method is disclosed for filling a hole in a sample surface by forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole by passing an ion beam current of 1 nA or higher to the hole having a depth larger than the diameter of the opening of the hole or the length of a longest side of the hole, setting the area scanned with the ion beam to almost the same as the opening area of the hole, and controlling the scanning area so as to move with respect to the position of the hole.

According to the method, a method is provided for filling, at high speed, a hole from which a sample has been extracted with an FIB. Particularly, since a high ion beam current is used, a hole filling method is provided in which an ion beam scanning area can be easily set.

(6) A method is provided for filling a hole in a sample surface by forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole while monitoring a change in luminance of a secondary electron image detected by irradiation with the ion beam, and while managing a movement amount and movement time of the scanning area.

According to the method, a method is provided for filling, at high speed, a hole from which a sample has been extracted with an FIB and, particularly, a hole filling method is provided in which an ion beam scanning area is moved efficiently.

(7) A substrate inspecting and analyzing method of irradiating a substrate with an ion beam is provided to process a surface of the substrate and for inspecting or analyzing the processed part or extracting a part of the substrate by a processing method using an ion beam, and inspecting/analyzing the extracted micro sample, wherein a hole formed by being irradiated with an ion beam on the substrate is filled with an energy-induced gas-assisted deposition layer, and a liquid material is applied on the gas-assisted deposition layer.

According to the method, a novel inspection and analysis method is provided in which the substrate for evaluation is not discarded uselessly and, even when a wafer from which a sample for inspection has been extracted is put back into a process, a defect is not caused. Particularly, the hole can be filled to have a flat surface, a foreign matter is not easily generated, and an influence due to contamination by ion species can be also reduced.

(8) A substrate inspecting and analyzing method of irradiating a substrate with a gallium focused ion beam is provided to process a surface of the substrate and for inspecting or analyzing the processed part or extracting a part of the substrate by a processing method using a gallium focused ion beam and inspecting/analyzing the extracted micro sample, wherein a hole formed by being irradiated with the gallium focused ion beam on the substrate is filled with a gallium focused ion beam induced gas-assisted deposition layer, a liquid material is applied on the gas-assisted deposition layer and cured and, after that, the substrate surface is cleaned to remove gallium.

According to the method, a novel inspection and analysis method is provided in which the substrate for evaluation is not discarded uselessly and, even when a wafer from which a sample for inspection has been extracted is put back into a process, a defect is not caused. Particularly, the hole can be filled to have a flat surface, foreign matter is not easily generated, and an influence due to contamination by ion species can be reduced also in an area around the hole.

(9) A substrate inspecting and analyzing method of irradiating a substrate with an ion beam is provided to process a surface of the substrate and for inspecting or analyzing the processed part or extracting a part of the substrate by a processing method using an ion beam and inspecting/analyzing the extracted micro sample, wherein a block member is inserted into a hole formed by being irradiated with an ion beam on the substrate.

According to the method, a novel inspection and analysis method is provided in which the substrate for evaluation is not discarded uselessly and, even when a wafer from which a sample for inspection has been extracted is put back into a process, a defect is not caused. Particularly, the hole can be filled with high throughput.

(10) A substrate inspecting and analyzing method of irradiating a substrate with a focused ion beam is provided to process a surface of the substrate and for inspecting or analyzing the processed part or extracting a part of the substrate by a processing method using a focused ion beam and inspecting/analyzing the extracted micro sample, wherein a hole formed by being irradiated with an ion beam on the substrate is filled with a focused ion beam-induced gas-assisted deposition layer, and the gas-assisted deposition layer is covered with a gaseous element species ion beam induced gas-assisted deposition layer.

According to the method, a novel inspection and analysis method is provided in which the substrate for evaluation is not discarded uselessly and, even when a wafer from which a sample for inspection has been extracted is put back into a process, a defect is not caused. Particularly, the hole can be filled to have a flat surface, foreign matter is not easily generated, and an influence due to contamination by ion species can be also reduced.

(11) A substrate inspecting and analyzing method of irradiating a substrate with a focused ion beam is provided to process a surface of the substrate and for inspecting or analyzing the processed part or extracting a part of the substrate by a processing method using a focused ion beam and inspecting/analyzing the extracted micro sample, wherein a hole formed by being irradiated with an ion beam on the substrate is filled with a focused ion beam-induced gas-assisted deposition layer, and the gas-assisted deposition layer is covered with a laser beam induced gas-assisted deposition layer.

According to the method, a novel inspection and analysis method is provided in which the substrate for evaluation is not discarded uselessly and, even when a wafer from which a sample for inspection has been extracted is put back into a process, a defect is not caused. Particularly, the hole can be filled to have a flat surface, foreign matter is not easily generated, and an influence due to contamination by ion species can be also reduced.

(12) An electronic device manufacturing method includes: a step of, after a step of an arbitrary process of fabricating a circuit pattern on a substrate, irradiating the substrate with an ion beam to process the surface of the substrate and inspecting or analyzing the processed part, or a step of extracting a part of the substrate by using at least an ion beam after the step of the process; a step of filling a hole formed by irradiating the substrate with the ion beam by energy-induced gas-assisted deposition and applying a liquid material on the gas-assisted deposition layer; and a step of putting the substrate back into the process for fabricating the circuit pattern.

According to the method, a novel electronic device manufacturing method is provided in which the substrate is not discarded for evaluation uselessly and, even when a wafer from which a sample for inspection has been extracted is put back into the process, a defect is not caused.

(13) An electronic device manufacturing method includes: a step of, after a step of an arbitrary process of fabricating a circuit pattern on a substrate, irradiating the substrate with an ion beam to process the surface of the substrate and inspecting or analyzing the processed part, or a step of extracting a part of the substrate by using at least an ion beam after the step of the process; a step of filling a hole formed by irradiating the substrate with the ion beam by energy-induced gas-assisted deposition and covering the gas-assisted deposition layer with a gaseous element species ion beam or laser beam induced gas-assisted deposition layer; and a step of putting the substrate back into the process for fabricating the circuit pattern.

According to the method, a novel electronic device manufacturing method is provided in which the substrate is not discarded for evaluation uselessly and, even when a wafer from which a sample for inspection has been extracted is put back into the process, a defect is not caused.

(14) An instrument is provided for fabricating and observing a substrate, for irradiating a substrate with an ion beam to process the surface of the substrate and for observing the processed part, or extracting a part of the substrate by a processing method using a focused ion beam to obtain a micro sample for inspection and analysis, wherein the instrument has a function of filling a hole formed by irradiating the substrate with the ion beam by filling the hole with a focused ion beam induced gas-assisted deposition layer and covering the gas-assisted deposition layer with a gaseous element species ion beam or laser beam induced gas-assisted deposition layer.

According to the instrument, a novel instrument is provided for fabricating and observing a substrate, capable of preparing a sample for a novel inspection and analysis method in which the substrate is not discarded for evaluation uselessly and, even when a wafer from which a sample for inspection has been extracted is put back into the process, a defect is not caused. Particularly, the instrument for fabrication and observation can fill the hole to have a flat surface at high throughput, does not allow foreign matter to be easily generated, and can reduce an influence due to contamination by ion species.

(15) An instrument is provided for fabricating and observing a substrate, for irradiating a substrate with an ion beam to process the surface of the substrate and for observing the processed part, or extracting a part of the substrate by a processing method using a focused ion beam to obtain a micro sample for inspection and analysis, wherein the instrument has a function of filling a hole formed by irradiating the substrate with the ion beam by filling the hole with a focused ion beam induced gas-assisted deposition layer and covering the gas-assisted deposition layer with a gaseous element species ion beam or laser beam induced gas-assisted deposition layer, and a focused ion beam emission axis and a gaseous element species ion beam emission axis or laser beam emission axis are offset from each other.

According to the instrument, a novel instrument is provided for fabricating and observing a substrate, capable of preparing a sample for a novel inspection and analysis method in which the substrate for evaluation is not discarded uselessly and, even when a wafer from which a sample for inspection has been extracted is put back into the process, a defect is not caused. Particularly, the instrument for fabrication and observation can fill the hole to have a flat surface at high throughput, does not allow foreign matter to be easily generated, and can reduce an influence due to contamination by ion species.

In any of (1) to (15), the sample is any of a silicon semiconductor wafer, an epitaxial growth silicon wafer, a wafer having a silicon thin film formed on a substrate, a compound semiconductor wafer, and a magnetic head integrated wafer. The electronic device is any of a silicon semiconductor device, a compound semiconductor device, a head for magnetic recording and reproduction, and a head for magnetooptical recording and reproduction. The inspection is conducted by using at least one of a transmission electron microscope, a scanning transmission electron microscope, a scanning electron microscope, and a scanning probe microscope. The analysis is conducted by analyzing an element by using at least one of an electron beam, an ion beam, and an x-ray and comparing the result with at least one of element distribution, element concentration, impurity distribution, and impurity concentration of a predetermined reference, thereby determining whether a sample is good or not. By the analysis, it is clarified whether the predetermined area is out of range of at least one of the predetermined reference shape, dimension, element distribution, element concentration, impurity distribution, and impurity concentration. Data obtained in the step of performing at least one of the monitoring, inspection, and analysis is stored at least in a computer.

DETAILED DESCRIPTION OF THE PREFERRED EMBODIMENTS

Figure 1:
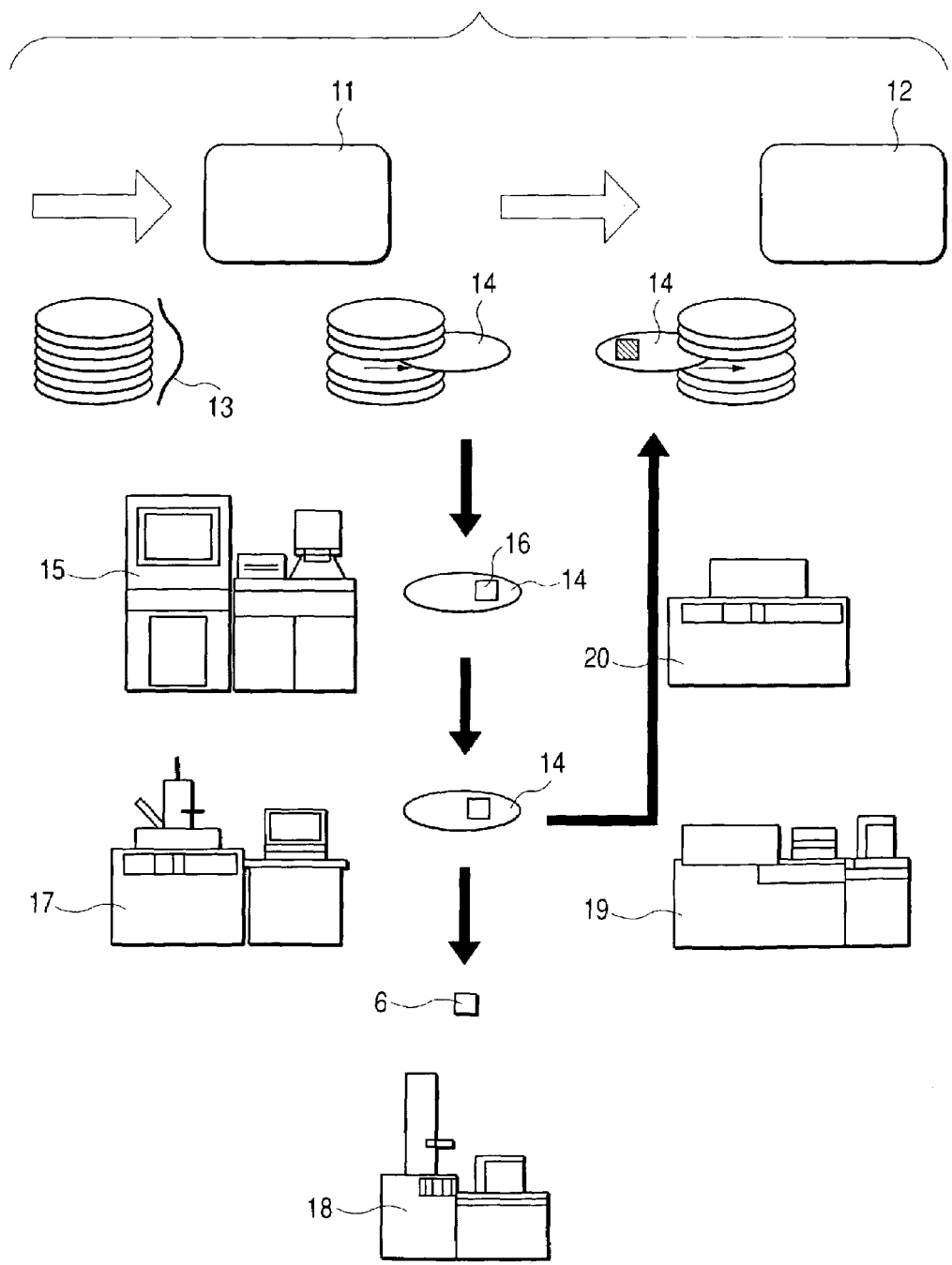
FIG. 1 is a diagram for explaining an example of the flow of a wafer in a process in an electronic device manufacturing method according to the invention.
Figure 2A:
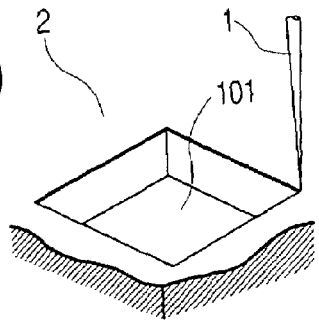
FIGS. 2A to 2G are diagrams for explaining the flow of extracting a micro sample from a sample in accordance with a conventional method.
Figure 2B:
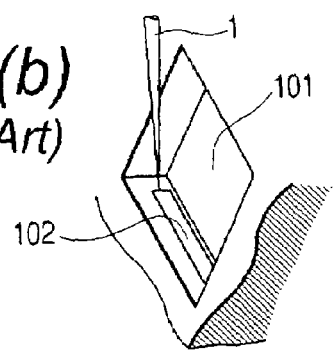
Figure 2C:
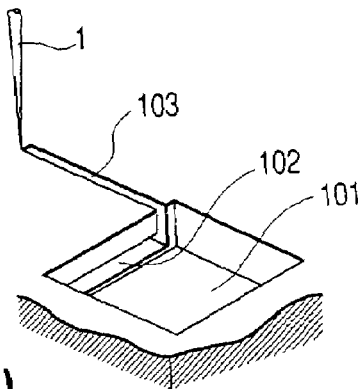
Figure 2D:
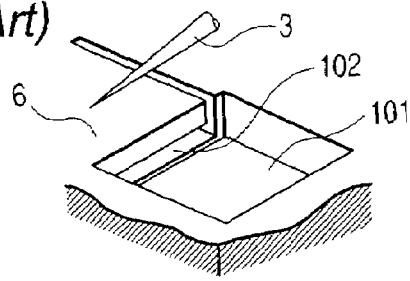
Figure 2E:
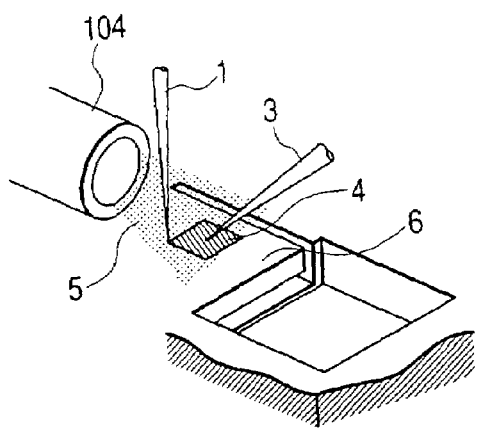
Figure 2F:
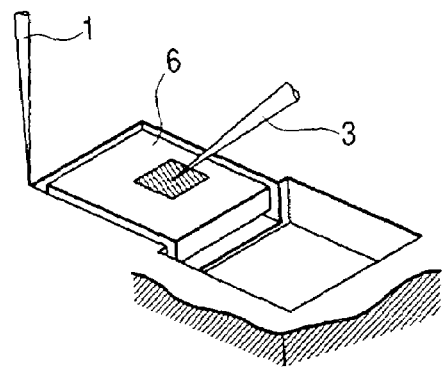
Figure 2G:
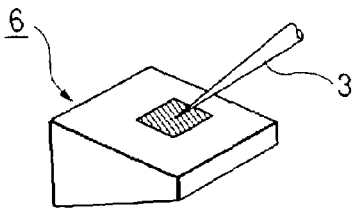

In an embodiment of a method of filling a hole from which a sample is taken out by using an FIB in accordance with the present invention, a part including the substrate surface of a sample is extracted with an FIB or a cross section is formed after a certain process, the progress of the process is inspected or analyzed by using the part including the substrate surface or the cross section, and the hole from which the part is taken out or opened for forming the cross section is filled at high speed.

An electronic device manufacturing method according to the invention for forming an electronic device by performing a plurality of processes on a sample includes a step of inspecting or analyzing the progress of the process with respect to a part including the surface of a substrate or a cross section, and a step of filling the hole from which the part is taken out or which is used to form the cross section, and the substrate is put back into the process line and a circuit pattern is fabricated.

First Embodiment

The basic flow of an electronic device manufacturing method including inspection and analysis methods of the invention will be described with reference to FIG. 1 with respect to the flow of a wafer.

First, a lot 13 consisting of a plurality of wafers is subjected to an arbitrary Nth process 11. Next, a wafer 14 for inspection is selected from the plurality of wafers and the other wafers enter a standby mode. The selected wafer 14 for inspection is introduced to an electron microscope 15 for inspection. When a failure is found here, the position of the failure is recorded as an address, and the information is sent to an instrument 17 for fabrication and observation. In the instrument 17 for fabrication and observation, a micro sample 6 including an area to be inspected is extracted from the wafer 14 for inspection by using a gallium FIB 1, a probe 3 (see FIG. 3 below) attached to the tip of a manipulator, a deposition layer fabricated by a deposition gas $W(CO)_6$, and the like.

The wafer 14 for inspection from which the micro sample 6 has been extracted is returned to the lot 13 and subjected to the following (N+1)th process 12. The micro sample 6 is sent to an instrument 18 for analysis and analyzed with respect to predetermined inspection items. The present invention has an important feature that the micro sample 6 for analysis is extracted during the period from the Nth process to the (N+1)th process.

The (N+1)th process and subsequent processes performed on the semiconductor device including the processed area from which the micro sample 6 is taken out by the inspection become invalid and the semiconductor device does not become a product. However, the number of wafers does not decrease. That is, the number of wafers subjected to the Nth process and the number of wafers subjected to the (N+1)th process are the same. Semiconductor devices manufactured in the area except for the area from which the micro sample 6 is taken out are counted as products as long as they are non-defective devices.

During the above operations, however, the hole from which the micro sample is taken out becomes a problem in the case of putting the wafer back to the following process. Therefore, the hole from which the micro sample is taken out is filled.

First, a method of filling a hole formed by being irradiated with an ion beam on a wafer with an FIB induced gas-assisted deposition layer and applying a liquid material on the gas-assisted deposition layer by the instrument 17 for fabrication and observation will be described.

Figure 3A:
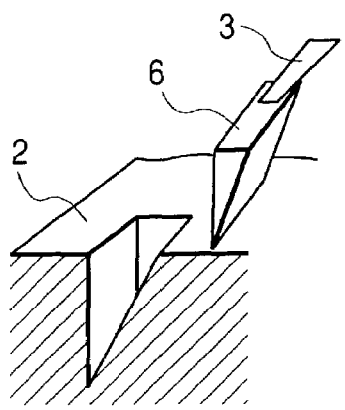
FIGS. 3A to 3D are diagrams showing the flow of an embodiment of the invention.
Figure 3B:
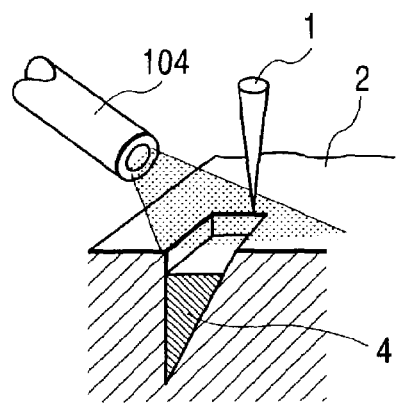

FIGS. 3A to 3D show the flow of the method. As shown in FIG. 3A, an operation for obtaining the micro sample 6 by using the gallium FIB 1 is the same as that in the conventional method and will be described in detail hereinlater. As shown in FIG. 3B, a sample wafer 38 is subjected to the following process. The hole formed by the irradiation with the FIB on the wafer is filled by FIB gas assisted deposition. The details of the operation will be also described hereinlater by using FIG. 6.

Figure 3C:
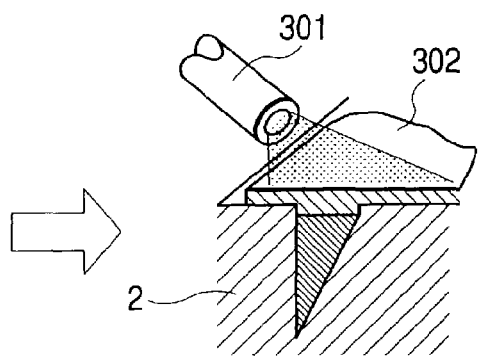
Figure 3D:
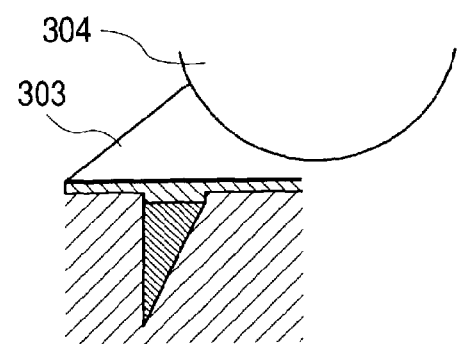

Subsequently, as shown in FIG. 3C, the wafer is taken out from the instrument 17 (FIG. 1) for fabrication and observation and introduced into a liquid injection instrument 19 (FIG. 1). A liquid material 302 is injected from a pipette 301 and applied on an area having a diameter of, for example, 1 mm so as to cover the area irradiated with the FIB. A protection film 303 made of the applied liquid material is formed by being baked by heating means. This method will be also described in detail later. As shown in FIG. 3D, an instrument 20 for wet cleaning cleans the wafer by, for example, brush cleaning using a brush 304 and a chemical, thereby removing gallium contamination on the outside of the liquid applied area.

Figure 4:
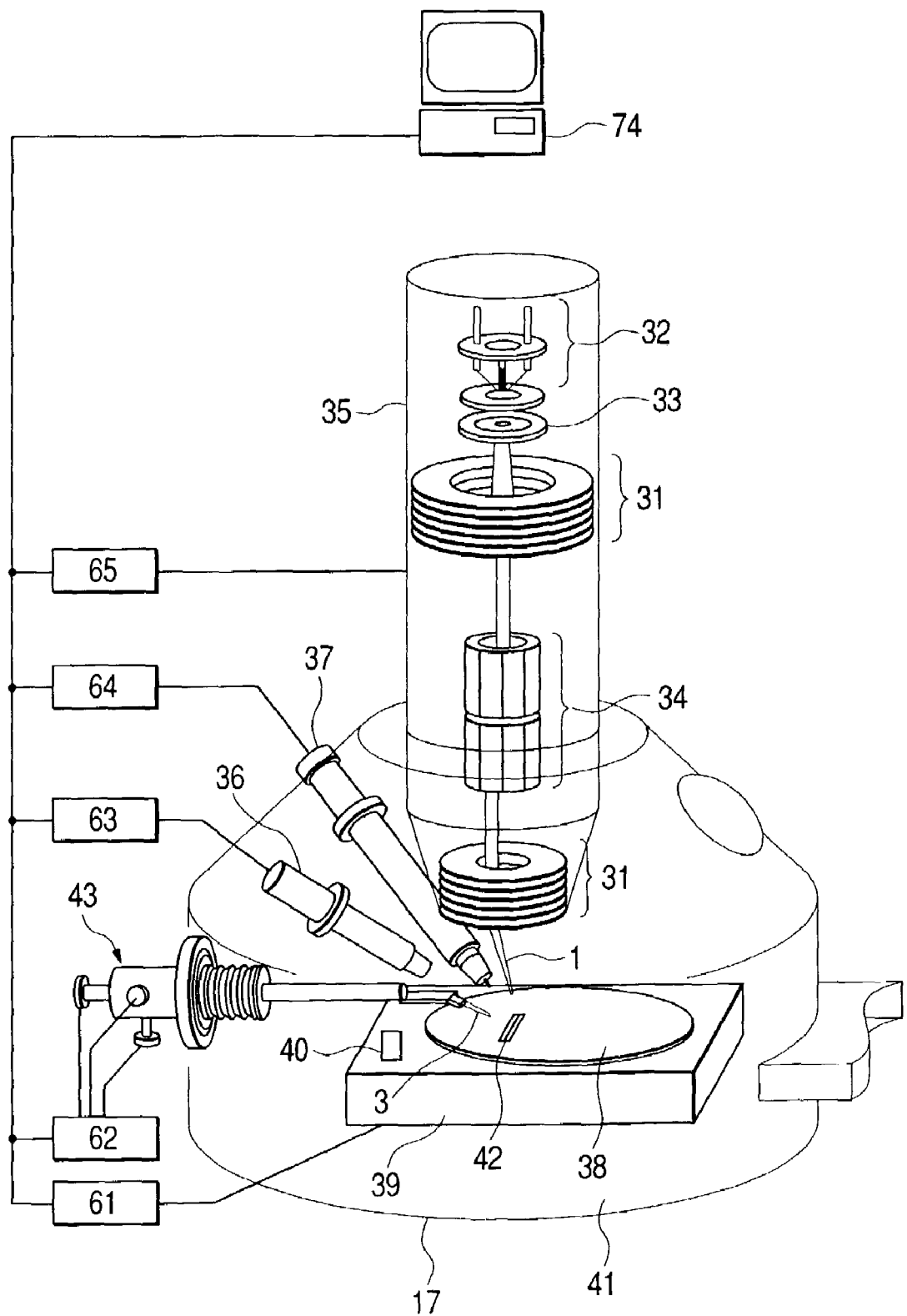
FIG. 4 is a diagram showing an instrument for fabrication and observation used for the embodiment of the invention.

FIG. 4 shows a schematic configuration of an instrument for fabrication and observation used for the method as an embodiment of the invention.

The instrument 17 for fabrication and observation has a vacuum chamber 41 in which there are an FIB irradiating optical system 35 constructed with a liquid metal ion source 32 for emitting gallium, a beam limiting aperture 33, an ion beam scanning electrode 34, an ion beam lens 31, and the like, a secondary electron detector 36 for detecting secondary electrons and secondary ions emitted from the sample irradiated with an FIB, a precursor gas dispenser 37 for supplying a material gas for forming a deposition layer in the ion beam irradiated area, the probe 3 attached to the tip of a manipulator 43, a specimen stage 39 on which the sample wafer 38 such as a semiconductor wafer or a semiconductor chip is placed, a sample holder 40 for fixing a micro sample extracted from the sample wafer, and the like. A stage controller 61, a manipulator driver 62, an amplifier 63 of the secondary electron detector, a controller 64 of the precursor gas dispenser, an FIB controller 65, a central processing unit 74, and the like, each taking the form of, mainly, an electric circuit and a computer are also disposed.

The operation of the instrument for fabrication and observation will now be described. First, the sample wafer 38 is irradiated with ions emitted from the liquid metal ion source 32 via the beam limiting aperture 33 and ion beam lens 33. The FIB 1 is converged from a diameter of about 1 micrometer to a few nanometers on the sample. When the sample wafer 38 is irradiated with the FIB 1, atoms constructing the sample surface are emitted to the vacuum by a sputtering phenomenon. Therefore, by using the ion beam scanning electrode 34 and scanning the FIB 1, processing at the level from micrometers to sub-micrometers can be performed.

By irradiating the sample wafer 38 with the FIB 1 while introducing the deposition gas into the sample chamber, a deposition layer can be formed. As described above, by skillfully using sputtering or deposition with the FIB 1, the sample wafer 38 can be processed. The deposition layer formed by irradiation of the FIB 1 is used to connect the contact portion at the tip of the probe 3 and the sample and to fix the extracted sample to the sample holder 40. The FIB 1 scans the sample, secondary electrons and secondary ions emitted from the sample are detected by the secondary electron detector 36, and the intensity is converted to luminance of an image, thereby enabling the sample wafer 38, probe 3, and the like to be observed.

The operation for fabricating the micro sample 6 by using the gallium FIB 1, which is the same as that of the conventional method, will now be described with reference to FIGS. 5A to 5J.

Figure 5A:
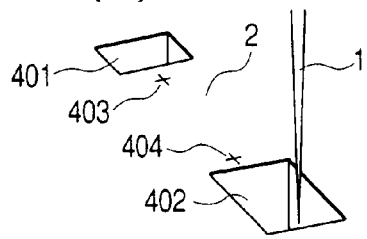
FIGS. 5A to 5J are diagrams for explaining the flow of extracting a micro sample from a sample.
Figure 5F:
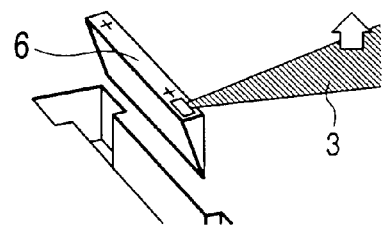
Figure 5B:
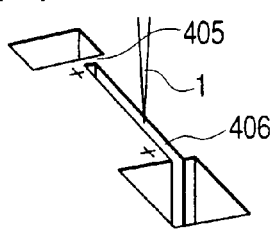
Figure 5G:
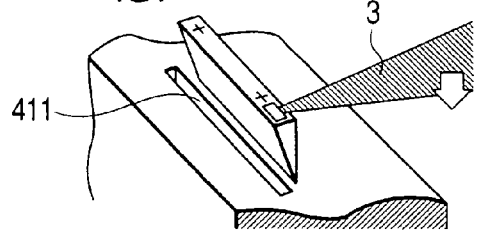
Figure 5C:
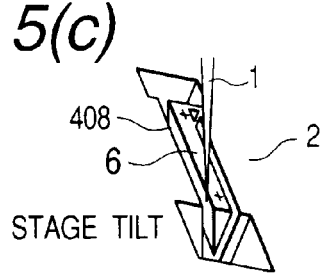
Figure 5H:
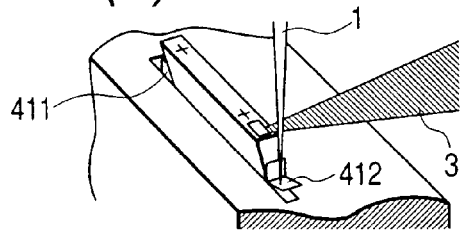
Figure 5D:
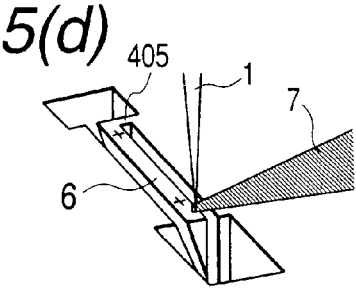

According to the method, as shown in FIGS. 5A to 5J, first, FIB 1 is emitted to form marks 403 and 404 for identifying a target position. After that, rectangular holes 401 and 402 are formed on both outer sides of the marks 403 and 404 in the sample 2 (FIG. 5A). A rectangular trench 406 is formed with the FIB 1 (FIG. 5B). The sample stage is tilted so that the sample surface is irradiated obliquely with the FIB 1 to form an oblique trench 408, thereby forming the micro sample 6 to be extracted which is connected with the sample 2 only via a supporting part 405 (FIG. 5C). The tilted sample stage is set to the original state, and the probe 3 is controlled by a probe controller so as to come into contact with a part of the micro sample 6 to be extracted. The supporting part 405 of the sample to be extracted will be cut later with an FIB. Since it is desired to cut the supporting part 405 in short time when a probe drift or the like is considered, the volume of the supporting part has to be small. Consequently, there is the possibility that the supporting part 405 is destroyed by the contact of the probe 3, so that the probe 3 is controlled to come into contact with the micro sample 6 while suppressing damage as much as possible by using a probe control method. The probe 3 and the micro sample 6 to be extracted which are in contact with each other are fixed by using a deposition layer 409 (FIG. 5D).

Figure 5I:
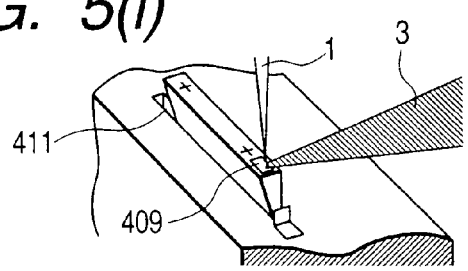
Figure 5E:
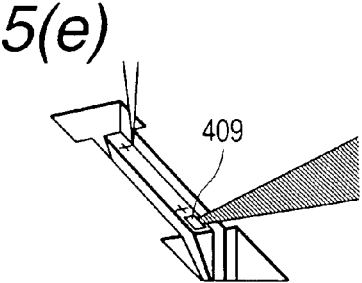
Figure 5J:
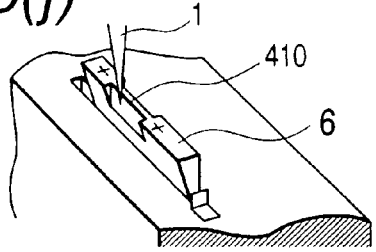

Subsequently, the supporting part 405 is cut with the FIB 1 (FIG. 5E). The micro sample 6 to be extracted is cut in such a manner and the probe 3 is lifted by the probe controller to extract the micro sample 6 (FIG. 5F). The cut-out micro sample 6 is made to come into contact with a trench 411 formed in a sample holder (FIG. 5G). The micro sample 6 has to come into contact with the trench 411 at a sufficiently low speed so that the micro sample 6 is neither destroyed, nor comes off the deposition layer 409 and is lost. After the micro sample 6 comes into contact with the trench 411, the micro sample 6 and the trench 411 are fixed to each other by using a deposition layer 412 (FIG. 5H). After being fixed, the connection part of the probe 3 is irradiated with an FIB, sputtering is performed, and the probe 3 is separated from the extracted micro sample 6 (FIG. 5I). In the case of using the micro sample 6 as a TEM sample, finally, an observation area 410 is thinned to a thickness of 100 nm or less by being irradiated with the FIB 1 again (FIG. 5J).

An operation of filling the hole formed by extracting the micro sample 6 by FIB gas assisted deposition will be described with reference to FIGS. 6A and 6B.

First, the deposition gas 5 is supplied from the nozzle 104 for delivering gas, a scanning area 1002 of the FIB 1 is set as large as the area of an opening of the hole, and only the inside of a hole 1001 is irradiated with the FIB 1. By the operation, a deposition layer 4 is formed on the side walls and the bottom face of the hole 1001. Subsequently, the FIB is moved in the direction apart from two walls out of four walls as shown by the arrow of FIG. 6A so that a part of the scanning area 1002 overlaps with the hole, that is, a part of the side walls of the hole is irradiated with the FIB and a part of the side walls is not irradiated with the FIB. Concretely, two walls out of four walls are irradiated with the FIB and the side wall, that is, the deposition layer 4 formed on the other two walls is not irradiated with the FIB. Consequently, sputter particles emitted from the side walls irradiated with the FIB are re-attached to the two side walls which are not irradiated with the FIB and deposition in the side wall direction is accelerated.

The scanning area 1002 is sequentially moved and the movement is finished in a state where the scanning area 1002 is not overlapped with the hole. That is, the hole is filled by growing the deposition layer mainly from the direction of the side wall of the hole as schematically shown in FIG. 6B. Although the deposition layer is formed also on the bottom face in practice, for easier understanding, it is not shown in FIG. 6B. When the deposition layer 4 is deposited and the hole is almost filled up, the supply of the deposition gas 5 is stopped.

Figure 7A:
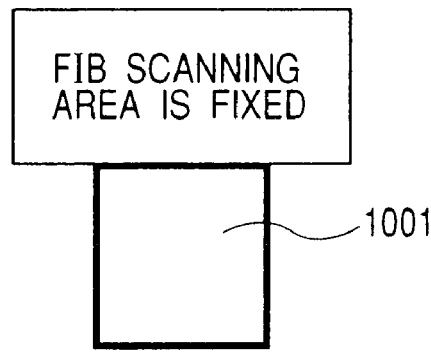
FIGS. 7A and 7B are schematic diagrams showing a conventional method of filling a hole.
Figure 7B:
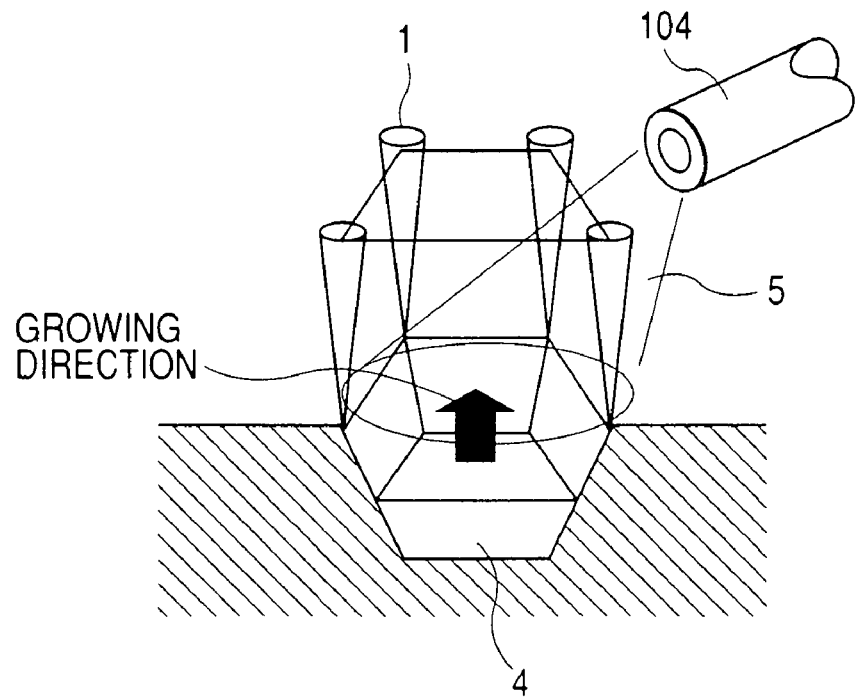
Figure 8A:
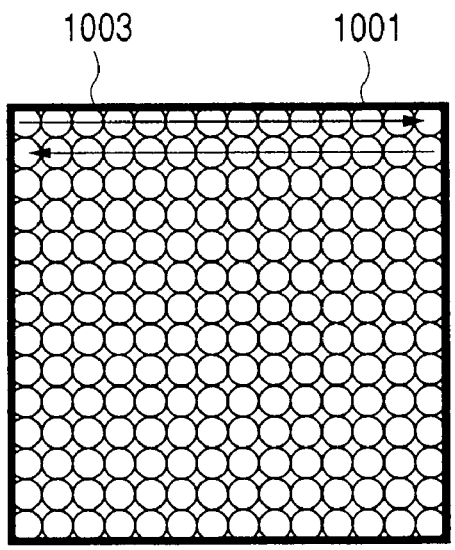
FIGS. 8A to 8D are schematic diagrams showing another example of the method of filling a hole at high speed according to the invention.
Figure 8B:
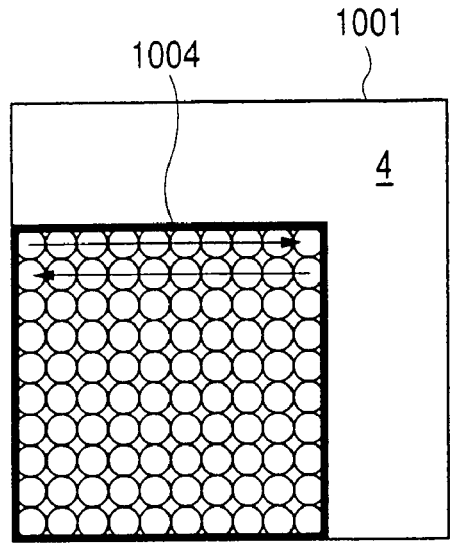
Figure 8C:
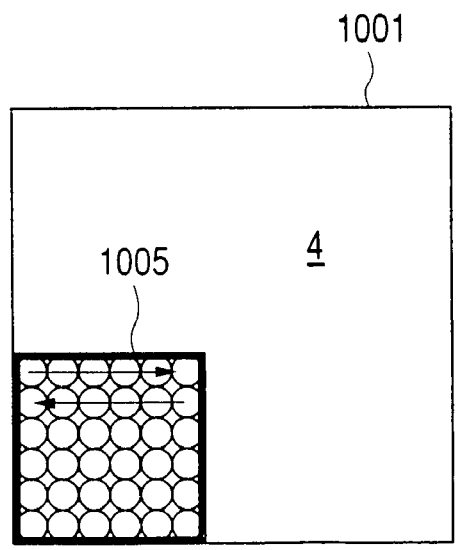
Figure 8D:
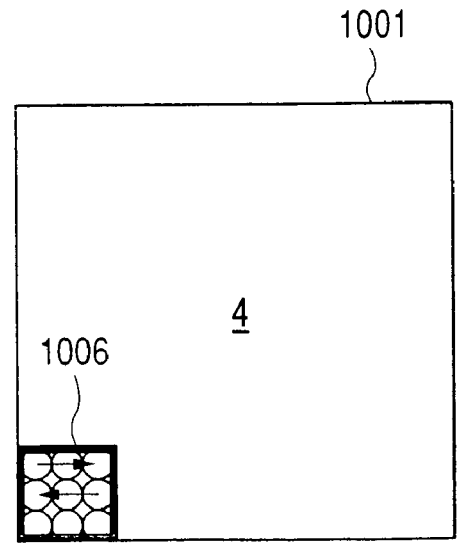

Conventionally, the scanning area of the FIB 1 is set as large as the opening area of the hole, and the inside of the processed hole 1001 is continuously irradiated with the FIB 1 without moving the FIB. 1. The deposition layer 4 is grown, as schematically shown in FIG. 7B, mainly from the bottom face. In order to fill the hole at high speed, the absolute amount of the deposition layer increases in proportion to the FIB current. Consequently, to increase the speed of filling the hole, it is advantageous to increase the FIB current. However, in the conventional method, if the FIB current is increased to a high current of about 1 nA or higher, the deposition efficiency deteriorates and the deposition amount and the sputtering amount become about the same. The growth of the deposition layer is stopped, so that the hole cannot be filled at high speed. According to the method of the invention, however, even when the ion beam current is set to 1 nA or higher, the side wall, once grown, is not irradiated with the FIB, but instead, by the re-attachment of the sputter particles from the opposite side wall, a high-speed hole filling operation is realized.

Figure 6A:
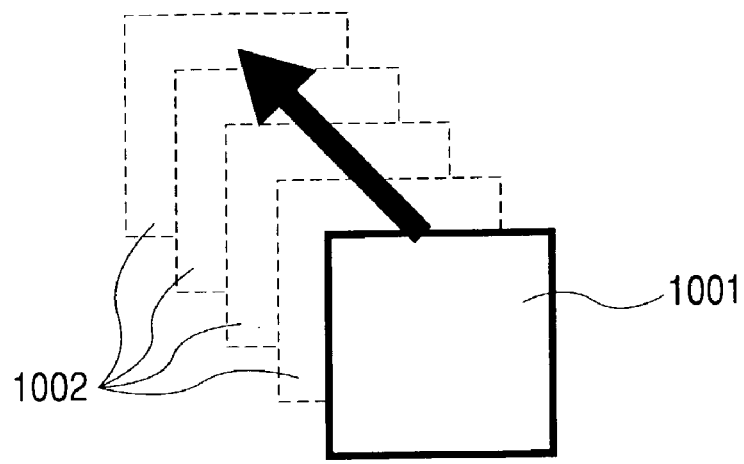
FIGS. 6A and 6B are schematic diagrams for explaining a basic configuration of a method of filling a hole at high speed according to an embodiment of the invention.
Figure 6B:
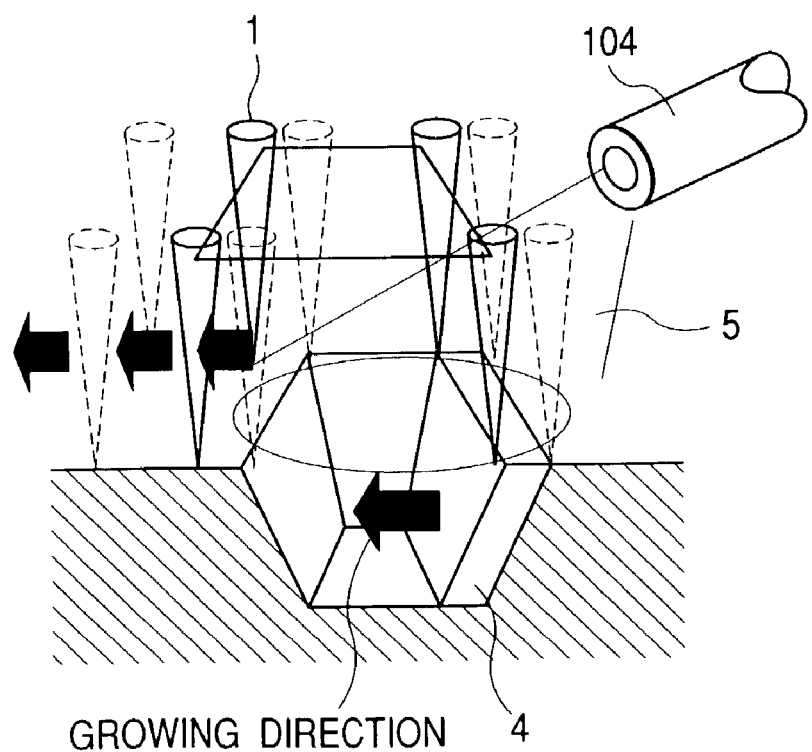

Although the scanning area 1002 is moved so as to cross the hole in the embodiment of FIGS. 6A-6B, a method of moving the scanning area as shown by FIGS. 8A to 8D may be also employed. In FIGS. 8A to 8D, circles indicate irradiation points of the FIB. In order of FIGS. 8A, 8B, 8C, and 8D, the scanning area is moved from scanning area 1003 so as to be apart from two walls out of four walls as sequentially shown by scanning areas 1004, 1005, and 1006. In such a manner, a deposition layer 4 grown on a wall at the time of the scanning area 1003 is not irradiated with the FIB when the scanning area is moved to 1004. By reattachment of sputter particles from the opposite side wall, growth of the deposition layer 4 from the two walls continues. Thus, high-speed hole filling operation is realized.

Figure 9A:
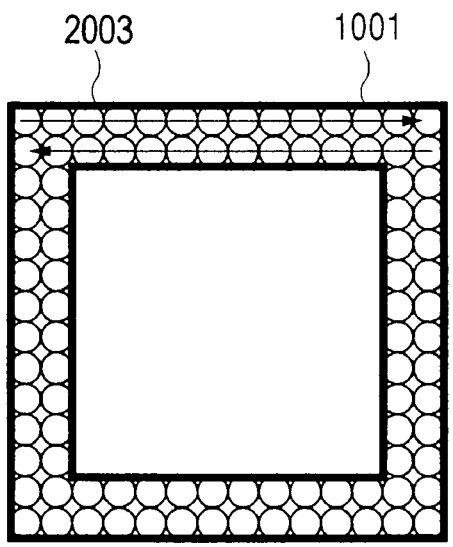
FIGS. 9A to 9D are schematic diagrams showing further another example of the method of filling a hole at high speed, according to the invention.
Figure 9B:
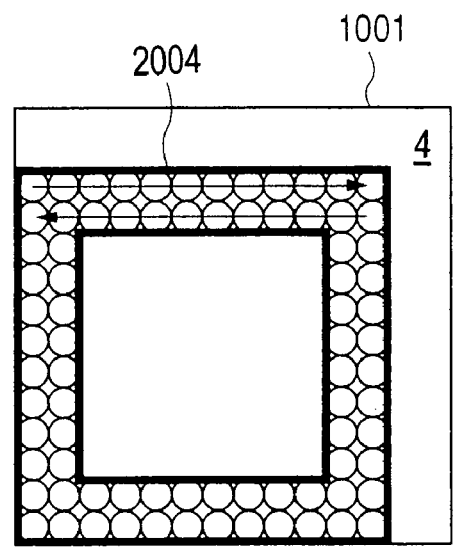
Figure 9C:
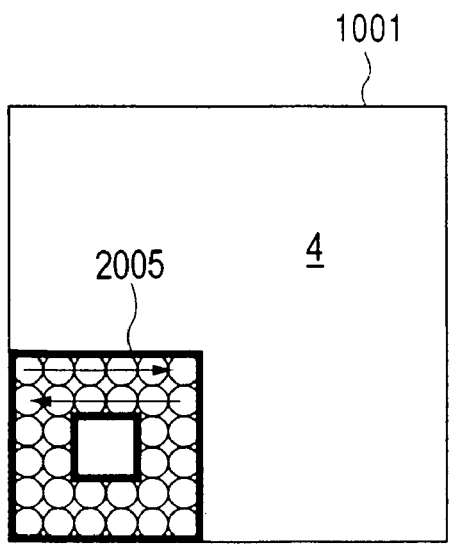
Figure 9D:
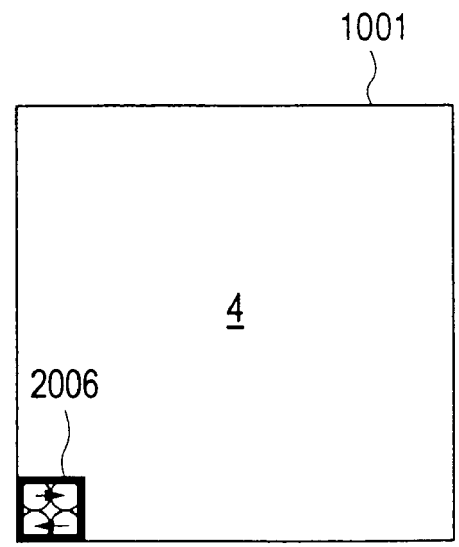

The following method as shown in FIGS. 9A to 9D may be also employed. Specifically, the FIB irradiation density is set to be almost constant in the FIB scanning area. The scanning area is controlled so that the scanning area is continuously reduced with respect to the position of the hole, while a deposition layer 4 is formed in the hole. In FIGS. 9A to 9D, circles indicate FIB irradiation points. FIG. 9A illustrates the first scanning area 2003, and FIG. 9B shows a reduced scanning area 2004. The other conditions of the irradiation area shown by scanning area 2004 are almost the same as those of the imaginary irradiation first scanning area 2003. During the scanning, the area outside of the scanning area 2004 is not scanned, so that the sample is not irradiated with the FIB. The scanning area is irradiated similarly also in the case where the scanning area is reduced to scanning area 2005 shown in FIG. 9C and to scanning area 2006 shown in FIG. 9D. In such a manner, the deposition layer 4 grows from two walls so that the hole can be filled more efficiently at higher speed.

When the scanning area is simply reduced, the current density of the FIB increases effectively and the hole filling condition changes, so that it consequently becomes difficult to perform the hole filling control. Therefore, when the scanning area is reduced, an imaginary scanning area to be set is fixed and the area of the sample which is intended to not be irradiated due to the reduction is controlled so as to not to be irradiated with the FIB. In such a manner, while maintaining the effective current density constant, the scanning area can be reduced and the hole filling control can be performed. In this way, the FIB irradiation time in each of the scanning areas can be set constant.

The hole filling method can be utilized particularly for a hole having a large depth as compared with the diameter or length of a longest side of the opening, that is, a so-called deep hole. Since the area of the side face is larger than that of the bottom face of the hole, the method of growing the deposition layer mainly from the side wall is more efficient.

In the hole filling method, in a secondary electron image formed according to the intensity of a secondary electron generated by scanning of the FIB 1, the luminance of the secondary electron image changes as the deposition layer grows around the wall after the hole filling operation is started. The change stops at the time when the growth of the deposition layer from the side wall reaches equilibrium. Therefore, in order to move the scanning area efficiently, by moving the scanning area by an amount of the area in which the luminance changes at a timing when the luminance change is finished, the hole filling operation can be performed efficiently without a loss. By programming such a setting in advance, the hole filling operation is automatically finished. It is also effective in the method of continuously reducing the area with respect to the position of the hole while the ion beam irradiation density is set to be almost constant.

A method of taking a wafer from the instrument 17 for fabrication and observation, introducing the wafer to the liquid injection instrument 19, and applying a liquid material so as to cover an area irradiated with an FIB will now be described.

As liquid materials, various complex solutions (for example, an application liquid for forming a silicon oxide film called "spin on glass" (abbreviated as SOG), epoxy resin solutions, polyimide precursor solutions, and the like can be applied. The material can be applied by using a micro pipette. A solid protection film is formed from the applied liquid material by baking which uses heating means such as various atmosphere furnaces, a hot plate, a laser, or the like, photo-curing using an ultraviolet lamp or ultraviolet emitting means for emitting an ultraviolet laser beam, or the like. After the baking, the wafer is cleaned by the instrument 20 for wet cleaning to remove the gallium contamination on the outside of the liquid applied area.

In the embodiment, the thickness of the film formed by heating is set to about 0.5 micrometer or less. It can largely reduce occurrence of a crack in the case of filling a hole having a depth at least a few micrometers with only a liquid material. Since most of the hole filling operation is performed with positional precision of 1 micrometer or less at the worst, a problem such that the surface rises at least a few micrometers from the hole, which occurs in the conventional hole filling method by argon ion beam irradiation deposition, does not occur.

Since the area irradiated with the FIB is covered with the oxide film, the possibility decreases for problems, such as that gallium evaporates in a vacuum in a following process, invades another semiconductor device, and causes a poor electrical characteristic or poor electrical contact. By using the hole filling operation with the FIB only, it is difficult to fill the hole so that the surface becomes at the same level as the surface of the wafer, and a roughness of about one micrometer often occurs. However, by the above method, a liquid material is further applied, so that the roughness is lessened. The hole filling operation is then able to realize a flatter surface.

Under this embodiment, the method is provided for filling, at high speed, the hole from which a micro sample has been taken out using an FIB. Further, an instrument is provided for fabricating and observing a wafer capable of forming a sample for a novel inspecting and analyzing method which does not uselessly discard a wafer for evaluation, and does not cause a defect even when a wafer from which a sample for inspection has been taken out is put back into the process line. An instrument is provided for fabricating and observing a wafer, by which foreign matter is not easily generated and an influence due to contamination by ion spices can be reduced.

Second Embodiment

Figure 10:
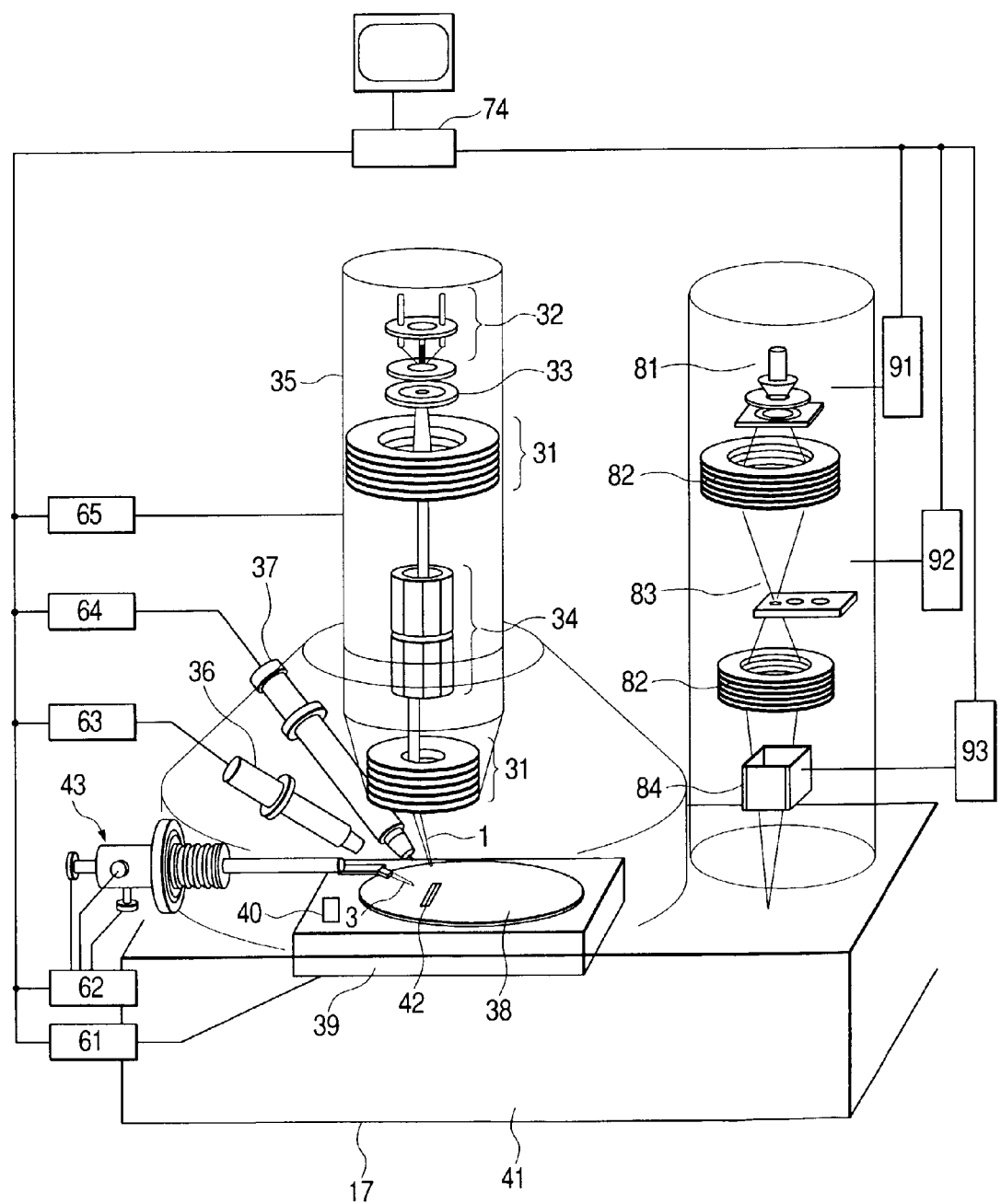
FIG. 10 is a diagram for explaining another embodiment of an instrument for fabrication and observation used for the invention.

FIG. 10 shows a schematic configuration of an instrument for fabrication and observation having a second ion beam irradiating instrument used for another embodiment of the invention.

The instrument 17 for fabrication and observation has a vacuum chamber 41. In a manner similar to the instrument for fabrication and observation of the first embodiment, in the vacuum chamber 41, the FIB irradiating optical system 35, secondary electron detector 36, precursor gas dispenser 37, probe 3, specimen stage 39, and the like are provided. In the instrument, a second ion beam irradiating system is installed and is constructed by a duoplasmatron 81 for emitting gas ions of gas element species of argon, oxygen, nitrogen, or the like, an ion beam lens 82, a beam limiting aperture 83, an ion beam scanning deflector 84, and the like.

As devices for controlling the instrument 17, there are disposed the stage controller 61, manipulator driver 62, amplifier 63 of the secondary electron detector, controller 64 of the precursor gas dispenser, FIB controller 65, the central processing unit 74, and, in addition, a controller 91 for duoplasmatron 81, a controller 92 for ion beam lens 82, a controller 93 for ion beam scanning, and the like. In the instrument, the FIB emission axis and the argon ion beam emission axis are offset from each other as shown in FIG. 10. There is consequently an advantage such that designing of instruments around the FIB irradiation system is facilitated.

The operation of the FIB irradiating optical system 35 is similar to that in the first embodiment. The processing operation for fabricating a micro sample by using the gallium FIB 1 is also similar to that of the conventional method. The micro sample 6 extracted from the instrument is analyzed by a tester.

However, only by the operations, the hole from which the micro sample 6 is taken out becomes a problem in the case of putting the wafer back to the following process. Consequently, the hole from which the micro sample 6 is taken out is filled.

In the embodiment, a method will be described of filling the hole formed by being irradiated with the gallium FIB 1 on the wafer with the gallium FIB 1 induced gas-assisted deposition film and, after that, covering the gallium FIB 1 induced gas-assisted deposition layer with a deposition layer by being irradiated with a broad argon ion beam whose beam diameter is on the order of one millimeter.

Figure 11A:
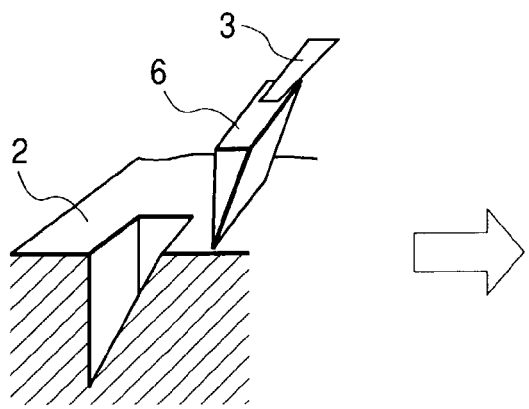
FIGS. 11A to 11D are diagrams showing the flow of the embodiment of the invention illustrated in FIG. 10.
Figure 11B:
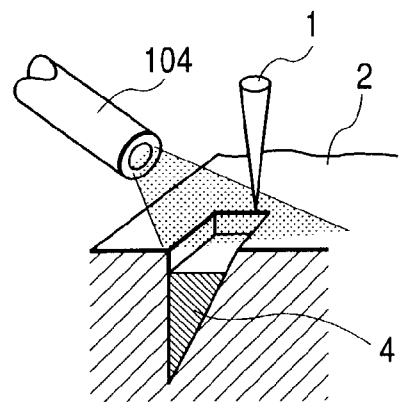

FIGS. 11A to 11D show the flow of the method. As shown in FIG. 11A, an operation for obtaining the micro sample 6 by using the gallium FIB 1 is the same as that of the conventional method. As shown in FIG. 11B, the sample wafer 38 is subjected to the following process. The hole formed by being irradiated with an ion beam on the wafer is filled with the gallium FIB 1 induced gas-assisted deposition layer. The operation is the same as that in the method described in the first embodiment.

Figure 11C:
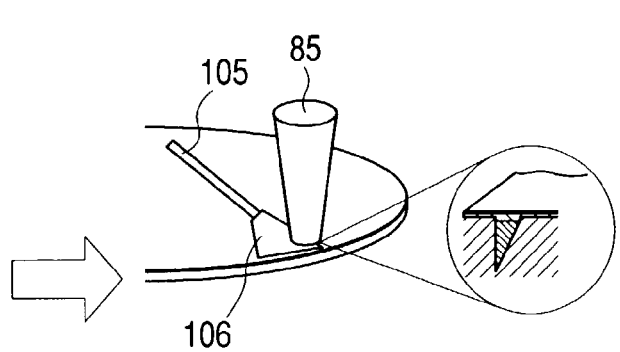

As shown in FIG. 11C, the wafer is taken out from the instrument 17 for fabrication and observation. In the instrument, the FIB emission axis and the argon ion beam emission axis are offset from each other, so that the specimen stage is moved so that the FIB induced gas-assisted deposition area comes directly below the argon ion beam emission axis. A precursor gas 106 for a silicon oxide film is supplied from another gas nozzle 105, and a broad argon ion beam 85 having a beam diameter of the order of one millimeter is emitted so as to cover almost the whole FIB hole filling area as a center, thereby forming a film having a thickness of about 0.5 micrometer. Since the FIB emission axis and the argon ion beam emission axis are offset from each other in this case, there is an advantage of a low risk that the deposition gas 5 is mixed in the operation of supplying the precursor gas 106 for the silicon oxide film.

Figure 11D:
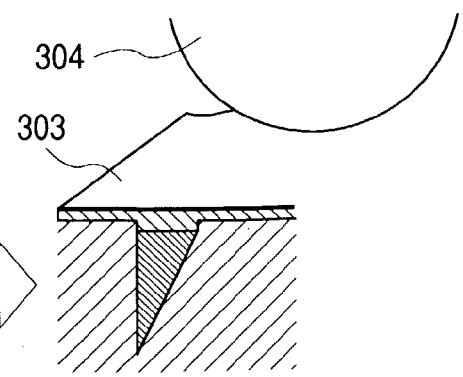

After that, as shown in FIG. 11D, the wafer is cleaned by so-called brush cleaning using, for example, the brush 304 and a chemical by the instrument 20 for wet cleaning, and the gallium contamination on the outside of the liquid applied area is removed.

An operation of forming an argon ion beam induced deposition layer after forming the deposition layer with the FIB will be described. An ion source of an argon ion beam irradiating instrument is the duoplasmatron 81, which emits argon ions in this case. An accelerating voltage of the ion beam 85 is 5 kV, an ion current is 2 micro amperes, and the beam diameter is adjusted to about 1 millimeter. An arbitrary position in the sample wafer 38 can be aimed at by the ion beam deflection electrode 84 and the area filled with the gallium FIB can be also aimed at and irradiated with the argon ion beam.

For the irradiation, the following preparation is made. First, the argon ion beam 85 is converged to a spot on a sample. After that, the specimen stage is moved and the spot-shaped irradiation trace is scanned with the FIB 1, secondary electrons are detected, and the spot-shaped irradiation trace is observed, thereby clarifying the relation between the argon ion beam irradiation position and the FIB 1 irradiation position. In the controller 93 for ion beam scanning of this instrument, the process position of the micro sample 6 and the gallium FIB irradiation condition information is stored. The process position is called from the stored information, the argon ion beam irradiating system is controlled, and the process position is automatically irradiated with the argon ion beam 85. The control is performed in a centralized manner by the centralized processing unit 74.

Although the argon ion beam is used in the illustrated embodiment, oxygen or nitrogen may alternatively be used. In place of the ion beam, a laser beam may be emitted. Since a deposition layer can be formed with a laser beam in short time, the laser beam is suitable to increase the throughput and process a wide area at once. On the other hand, the target position can be irradiated with the ion beam more precisely than a laser beam.

Although the argon ion beam instrument is assembled in the FIB ion beam instrument in this instrument, a removing work can be performed by a second ion beam irradiating instrument having performance equivalent to that of the argon ion beam irradiating instrument. In this case, process position information is transferred from the FIB ion beam instrument to the argon ion beam irradiating instrument, so that the process position can be automatically irradiated with an argon ion beam. In this case, however, the cost of two instruments is necessary, the work time is longer and, as a result, the cost of manufacturing devices becomes higher.

By the method as described above, the hole is filled with an FIB with high positional precision, so that the problem that occurs in a hole filling operation with only conventional argon ion beam irradiation, such as that the area around the hole rises, does not occur here. Since the area irradiated with the FIB is largely covered with an oxide film, there is a decreased possibility of problems occurring, such as that gallium diffuses in a following process and invades another semiconductor device, and causes a poor electrical characteristic or poor electrical contact. By the hole filling operation only with the FIB, it is difficult to fill the hole so that the surface becomes flush with the surface of the wafer, and roughness having a height of about one micrometer or less often occurs. However, by the method of this embodiment, the deposition film is more widely and thinly formed, so that local roughness is lessened. Thus a hole filling operation realizing a flatter surface is achieved.

According to the embodiment, the instrument for fabrication and observation is provided that is capable of preparing a sample for a novel inspecting and analyzing method which does not uselessly discard a wafer for evaluation and does not cause a defect even when a wafer from which a sample for inspection has been taken out is put back into a process lined. Particularly, an instrument for fabricating and observing a wafer is provided that is capable of filling a hole to have a flat surface and with high throughput, and by which foreign matter is not easily generated and an influence due to contamination by ion spices can be reduced.

Third Embodiment

Figure 12:
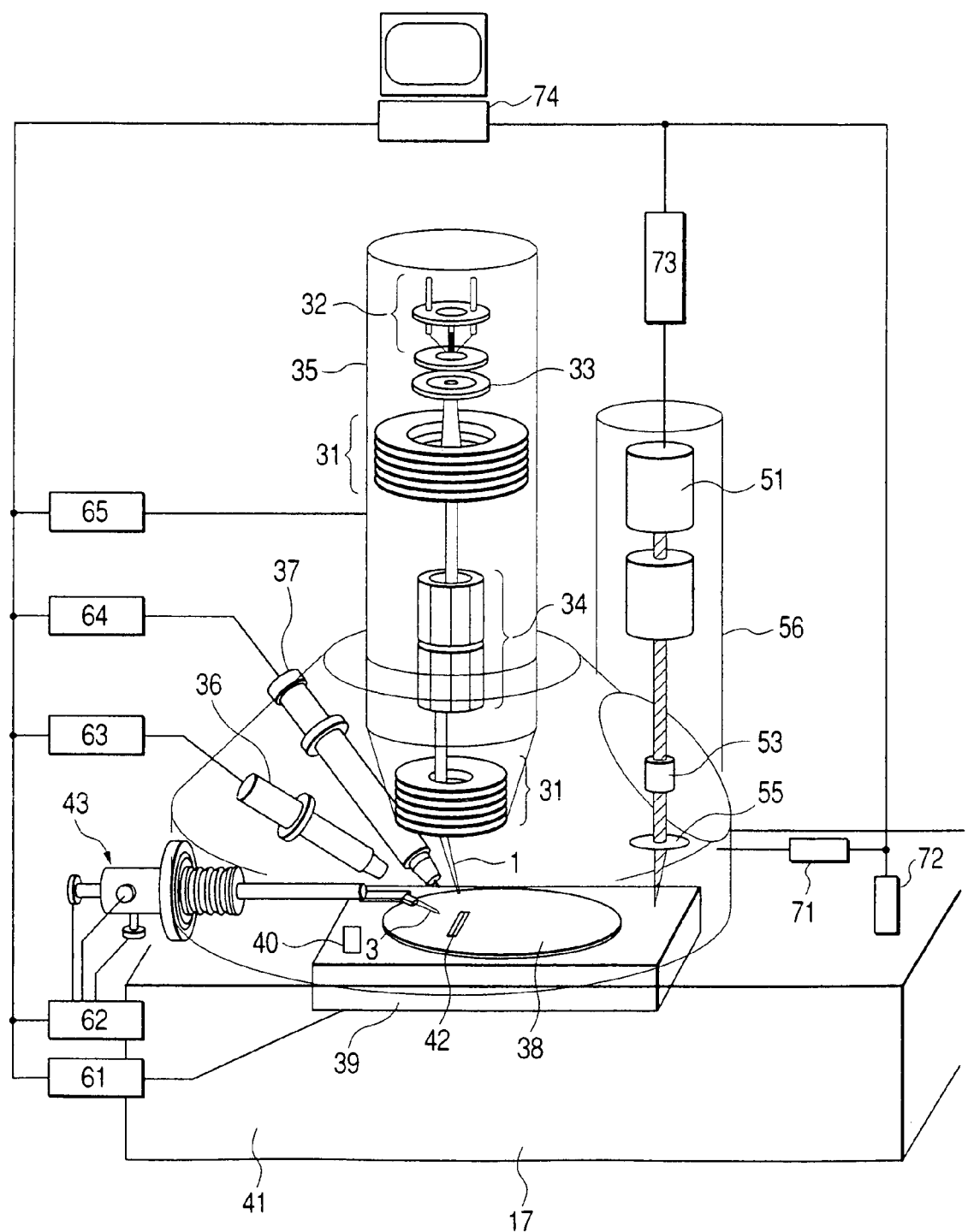
FIG. 12 is a diagram for explaining further another embodiment of the instrument for fabrication and observation for use in the invention.

FIG. 12 is a schematic configuration diagram of an instrument for fabrication and observation for use in yet another embodiment of the invention.

The instrument 17 for fabrication and observation of the third embodiment has the vacuum chamber 41 in which are disposed the FIB irradiating optical system 35 constructed by the liquid metal ion source 32 for emitting gallium, beam limiting aperture 33, ion beam scanning electrode 34, ion beam lens 31, and the like, secondary electron detector 36 for detecting secondary electrons and secondary ions emitted from the sample irradiated with the FIB, precursor gas dispenser 37 for supplying an original material gas for forming a deposition layer in the ion beam irradiated area, probe 3 attached to the tip of the manipulator 42, specimen stage 39 on which the sample wafer 38, such as a semiconductor wafer or a semiconductor chip, is mounted, sample holder 40 for fixing a micro sample as a part extracted from the sample wafer, and the like.

Further, a laser system 56 is constructed with a laser oscillator 51 and the like, an optical lens 55 for laser, and the like are attached. The laser system 56, the optical lens 55 for laser, and the like are fixed as one component to the vacuum chamber.

As devices for controlling the instrument 17, there are disposed the stage controller 61, manipulator driver 62, amplifier 63 of the secondary electron detector, controller 64 of the precursor gas dispenser, FIB controller 65, a controller 71 for laser mirror 53, a controller 72 for optical lens 55 of the laser system, a controller 73 for the laser system, the central processing unit 74, and the like each taking the form of an electric circuit or an arithmetic unit are disposed. In the instrument, the FIB emission axis and the laser beam emission axis are offset from each other as shown in FIG. 12. A sample can be moved from the FIB irradiation position to the laser beam irradiation position by moving the stage with precision of a few micrometers. There is consequently an advantage such that designing of instruments around the FIB irradiation system is facilitated by the offset function.

The operation of the FIB irradiating optical system 35 is similar to that of the first embodiment. The processing operation for fabricating a micro sample by using the gallium FIB 1 is also similar to that of the conventional method. The micro sample 6 extracted from the instrument is analyzed by a tester.

The sample wafer 38 is subject to the following process. The operation of filling the hole formed by being irradiated with an ion beam on the wafer with a gallium FIB 1 induced gas-assisted deposition layer is also similar to that of the first embodiment.

In the third embodiment, the gallium FIB 1 induced gas-assisted deposition layer is covered with a deposition layer formed by irradiation with a laser beam. First, in the instrument, since the FIB emission axis and the laser beam emission axis are offset from each other, the specimen stage is moved so that an FIB induced gas-assisted deposition area comes directly below the laser beam emission axis.

The operation of forming the deposition layer by irradiation of the laser beam after forming the FIB deposition layer will be described. In this case, a YAG laser is used as a laser system. A laser beam 57 emitted from the laser system 56 is led into the vacuum chamber toward the gallium FIB 1 induced gas-assisted deposition layer via the optical lens 55 for laser. While supplying the precursor gas 106 for a silicon oxide film from another gas nozzle 105, a laser beam is emitted so as to cover almost the whole FIB hole filling area as a center, thereby forming a film having a thickness of about 0.2 micrometer.

A laser beam irradiation trace is scanned with the FIB 1, secondary electrons emitted from the sample are detected by the secondary electron detector 36, and the laser beam irradiation trace is observed in advance, thereby clarifying the relation between the laser beam irradiation position and the ion beam irradiation position. For example, on the basis of process position information, an FIB hole filling area 42 can be automatically irradiated with the laser beam 57 in a micro semiconductor device formed on a silicon wafer. The control is performed in a centralized manner by the central processing unit 74. Since the FIB emission axis and the laser beam emission axis are offset from each other, there is an advantage such that the risk of mixture of the deposition gas 5 during the operation of supplying the precursor gas 106 for depositing a silicon oxide film is low.

According to the embodiment, an instrument for fabricating and observing a wafer is provided that is capable of forming a sample for a novel inspecting and analyzing method which does not uselessly discard a wafer for evaluation, and does not cause a defect even when a wafer from which a sample for inspection has been taken out is put back into a process. Particularly, an instrument for fabricating and observing a wafer is provided that is capable of filling a hole to have a flat surface and with high throughput, and by which foreign matter is not easily generated and an influence due to contamination by ion spices can be reduced.

As another embodiment according to the invention, a method of inserting a block member into a hole formed by being irradiated with an ion beam will be described. An instrument used in the embodiment is the same as the instrument 17 for fabrication and observation shown in FIG. 4.

The operation of the FIB irradiating optical system 35 is similar to that in the first embodiment, and a processing operation for fabricating a micro sample by using the gallium FIB 1 is the same as that in the conventional method. The micro sample 6 extracted by the instrument is analyzed by a tester.

A method will now be described for inserting a block member into a hole formed by being irradiated with an ion beam on the wafer from which the micro sample has been extracted.

First, a block member processed in a size suitable to be buried in the hole is preliminarily introduced into the vacuum chamber 41 and is set in an operation range of the probe 3 at the tip of the manipulator. The block member may be obtained by finely processing silicon, silicon oxide, or a metal such as aluminum or copper.

The manipulator is driven to make the tip of the probe 3 at the tip of the manipulator come into contact with the surface portion of the block member. While supplying the deposition gas 5 from the nozzle 104 for delivering gas, an area including the tip of the probe 3 is locally irradiated with the FIB 1, thereby forming the deposition layer 4. The block member and the tip of the probe 3 which are in contact with each other are connected via the deposition layer 4. In the case where the block member is fixed on a mounting stand or the like, the connection portion is cut by using the FIB 1 and a block member is cut out. The block member cut out is supported by the connected probe 3. Subsequently, the manipulator is driven to move the block member to a position over the hole and to a lower position, thereby inserting the block member into the hole.

After that, the deposition gas 5 is supplied from the nozzle 104 for delivering gas and an area including the gap between the block member and the hole is irradiated with the FIB 1, thereby forming the deposition layer 4. All of or a part of the gap between the block member and the hole is filled with the deposition layer 4. Subsequently, by irradiating the probe 3 with the FIB, the probe 3 is cut. This is a method of extracting a micro sample including a desired area to be analyzed from a sample, such as a wafer, to which a block member is connected by using the FIB and means for carrying the micro sample. By introducing the micro sample extracted by the method into various analyzers, analysis can be conducted.

By the method, a novel inspection and analysis method is provided by which a wafer is not uselessly discarded for evaluation and, even when a wafer from which a sample for inspection has been taken out is put back into a process line, a defect does not occur. Particularly, a hole can be filled with high throughput.

In the embodiment, the example of employing the method of extracting a micro sample by the instrument for fabrication and observation has been described. It is also possible to process the shape of a micro sample by an instrument for fabrication and observation, take the wafer out from the instrument for fabrication and observation, and extract a micro sample by another mechanism.

Figure 13A:
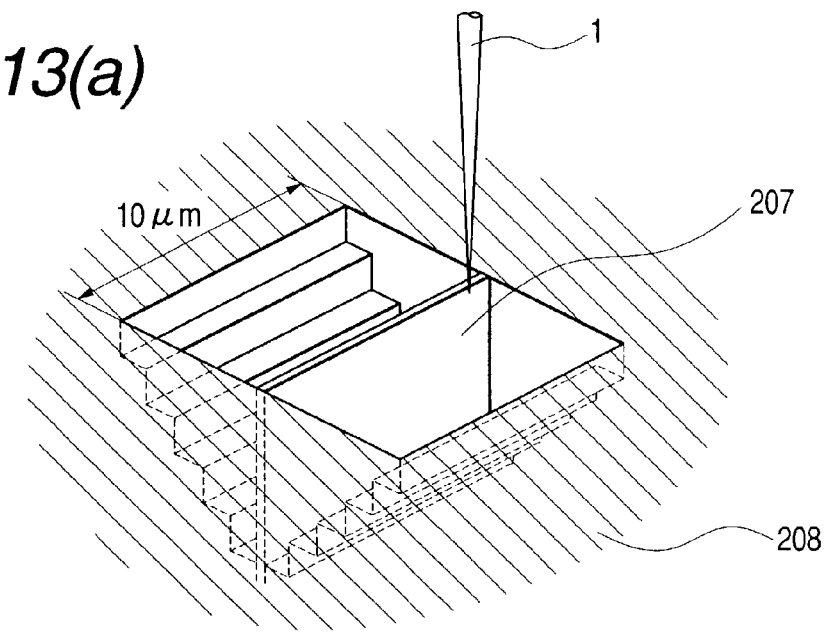
FIGS. 13A and 13B are diagrams for explaining another example of a sample fabricating method according to an electronic device fabricating method of the invention.
Figure 13B:
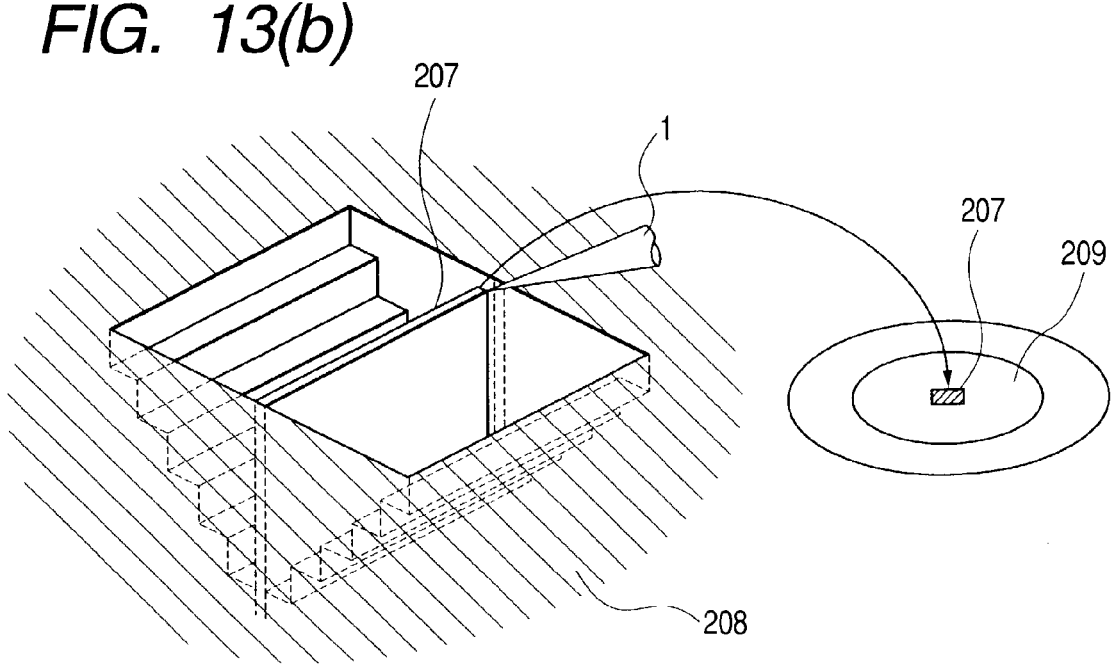

For example, as shown in FIG. 13A, a thin film 207 is formed on a wafer 208 and both sides of a target position are processed in a stair shape with the FIB 1, thereby fabricating a sample membrane 207. As shown in FIG. 13B, the peripheral portion of the sample membrane 207 is cut away by using the FIB 1 to cut the sample membrane 207 from the wafer 208. The wafer 208 is taken out from the instrument for fabrication and observation and, by using static electricity of a glass stick in atmosphere, the sample membrane 207 is moved from the wafer to a TEM sample holder 209.

The instrument of processing most of the outer shape of a micro sample with an ion beam in the instrument without taking the micro sample out is also included in the instrument for fabrication and observation of the invention. Not only the instrument for fabrication and observation of extracting a micro sample for analysis from a wafer as described above but also an instrument for fabrication and observation of forming a hole in a wafer with an FIB, observing the inside, such as a section of the device, by either an FIB or an electron beam emitted from an electron beam emitting system attached to the instrument, and analyzing the device are also included in the instrument for fabrication and observation of the invention.

As described in detail, according to the invention, a hole from which a sample has been extracted with an FIB can be filled at high speed. Further, a novel inspection and analysis method is provided by which a wafer is not discarded uselessly for evaluation and, even when a wafer from which a sample has been taken out for inspection is put back into a process, a defect does not occur. Particularly, a hole can be filled while realizing a flat surface with high throughput, foreign matter is not easily generated and an influence due to contamination by ion species can be reduced.

By using the manufacturing method of an electronic device according to the invention, a wafer can be evaluated without being cut, so that a new defect is not caused and an expensive wafer is not wasted. Thus, the manufacturing yield of an electronic device is improved. Further, the instrument for fabrication and observation is disclosed that is capable of realizing the inspection and analysis method and the electronic device manufacturing method.

Representative configuration examples of the invention are summarized as follows.

(1) A method of filling a hole by using an ion beam, including a step of irradiating a hole formed in a sample face with an ion beam to form an ion beam gas-assisted deposition layer in the hole, wherein the ion beam gas-assisted deposition layer is formed in the hole while controlling the ion beam so as to fall on a part of a side wall of the hole and so as not to fall on another part of the side wall in an area scanned with the ion beam.

(2) A method of filling a hole by using an ion beam, including: a step of processing a part of a sample surface with an ion beam; and a step of irradiating a hole formed in the sample face by the processing to form an ion beam gas-assisted deposition layer, wherein the ion beam gas-assisted deposition layer is formed by setting a range of an area scanned with the ion beam to be almost the same as an opening area of the hole in the sample face and controlling the scanning area so as to move with respect to the position of the hole.

(3) A method of filling a hole by using an ion beam, including: a step of processing a part of a sample surface with an ion beam; and a step of irradiating a hole formed in the sample face by the processing with the ion beam to form an ion beam gas-assisted deposition layer, wherein the ion beam gas-assisted deposition layer is formed in the hole while controlling the ion beam so that a part of a side wall of the hole is irradiated with the ion beam and another part is not irradiated in an area scanned with the ion beam and controlling the ion beam so as to continuously reduce the area scanned with lapse of time of filling the hole.

(4) In the above configuration, the hole has a structure such that an area of a side face is larger than that of a bottom face, and an ion beam current of 1 nA or higher is passed to the hole having the structure, thereby forming the ion beam gas-assisted deposition layer.

(5) In the above configuration, the ion beam gas-assisted deposition layer is formed in the hole while monitoring a change in luminance of a secondary electron image detected by irradiating the hole formed in the sample face with the ion beam and managing a movement amount and movement time of the scanning area.

(6) The above-described method further includes a step of, after forming the ion beam gas-assisted deposition layer in the hole, applying a liquid material on the ion beam gas-assisted deposition layer to thereby form a protection layer.

(7) The above-described method further includes a step of, after forming the ion beam gas-assisted deposition layer in the hole, covering the ion beam gas-assisted deposition layer with a gaseous element species ion beam gas-assisted deposition layer.

(8) The above-described method further includes a step of, after forming the ion beam gas-assisted deposition layer in the hole, covering the ion beam gas-assisted deposition layer with a laser beam gas-assisted deposition layer.

(9) An instrument for fabrication and observation by ion beam, includes: an ion gun; an optical system for converging and deflecting an ion beam emitted from the ion gun; means for irradiating a sample with the ion beam so as to be processed; a detector for detecting secondary particles emitted from the sample irradiated with the ion beam; means for forming an image by the detected secondary particles; and means for irradiating and scanning a hole formed in the surface of the sample to form an ion beam gas assisted deposition layer in the hole, wherein the ion beam gas assisted-deposition film is formed by controlling the ion beam so as to fall on a part of a side wall of the hole and so as not to fall on another part in an area scanned with the ion beam.

(10) An electronic device manufacturing method includes: a step of, after an arbitrary process in a manufacturing process of processing a sample and forming an electronic device, irradiating the sample with an ion beam to process a part of the surface of the sample for inspecting the sample; and a step of forming the ion beam gas assisted deposition film in a hole formed in the sample surface by the process while setting an area scanned with the ion beam to be almost the same as the opening area of the and controlling the area scanned with the ion beam so as to be moved with respect to the position of the hole, wherein the sample is inspected and, after that, the sample is put back into a process next to the arbitrary process and the manufacturing process is continued.

(11) A method is disclosed of filling a hole in a sample surface by forming an ion beam gas-assisted deposition layer in the hole by a charged particle beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the charged particle gas-assisted deposition layer is formed in the hole while controlling the ion beam so as to fall on a part of a side wall of the hole and so as not to fall on another part of the side wall in an area scanned with the charged particles.

(12) A method of filling a hole in a sample surface includes forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed by setting an area scanned with the ion beam to be almost the same as an opening area of the hole and controlling the scanning area so as to move with respect to the position of the hole.

(13) A method of filling a hole in a sample surface includes forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed while controlling the ion beam so that the area scanned with the ion beam is moved so as to be apart from at least a part of the side wall of the hole.

(14) A method of filling a hole in a sample surface includes forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole while controlling the ion beam so that a part of a side wall of the hole is irradiated with the ion beam and another part is not irradiated in an area scanned with the ion beam, and controlling the ion beam so as to continuously reduce the area scanned with lapse of time of filling the hole.

(15) A method of filling a hole in a sample surface includes forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole by passing an ion beam current of 1 nA or higher to the hole having a depth larger than the diameter of the opening of the hole or a length of a longest side of the hole, setting the area scanned with the ion beam to almost the same as the opening area of the hole, and controlling the scanning area so as to move with respect to the position of the hole.

(16) A method of filling a hole in a sample surface includes forming an ion beam gas-assisted deposition layer in the hole by an ion beam apparatus having an ion gun, a lens for converging an ion beam emitted from the ion gun, a deflector for scanning the ion beam, a controller of the deflector, a detector for detecting secondary particles generated from a sample irradiated with the ion beam, a gas gun for supplying a gas for ion beam gas-assisted deposition to the sample, a sample stage for holding the sample, and a sample position controller for controlling the position of the sample stage, wherein the ion beam gas-assisted deposition layer is formed in the hole while monitoring a change in luminance of a secondary electron image detected by irradiation with the ion beam and managing a movement amount and movement time of the scanning area.

(17) A substrate inspecting and analyzing method is provided for irradiating a substrate with an ion beam to process a surface of the substrate and inspecting or analyzing the processed part or extracting a part of the substrate by a processing method using an ion beam and inspecting/analyzing the extracted micro sample, wherein a hole formed by being irradiated with an ion beam on the substrate is filled with an energy-induced gas-assisted deposition layer, and a liquid material is applied on the gas-assisted deposition layer.

(18) A substrate inspecting and analyzing method is provided for irradiating a substrate with an ion beam to process a surface of the substrate and inspecting or analyzing the processed part or extracting a part of the substrate by a processing method using an ion beam and inspecting/analyzing the extracted micro sample, wherein a block-member is inserted into a hole formed by being irradiated with an ion beam on the substrate.

(19) A substrate inspecting and analyzing method is provided for irradiating a substrate with a focused ion beam to process a surface of the substrate and inspecting or analyzing the processed part or extracting a part of the substrate by a processing method using a focused ion beam and inspecting/analyzing the extracted micro sample, wherein a hole formed by being irradiated with an ion beam on the substrate is filled with a focused ion beam-induced gas-assisted deposition layer, and the gas-assisted deposition layer is covered with a gaseous element species ion beam induced gas-assisted deposition layer.

(20) A substrate inspecting and analyzing method is provided for irradiating a substrate with a focused ion beam to process a surface of the substrate and inspecting or analyzing the processed part or extracting a part of the substrate by a processing method using a focused ion beam and inspecting/analyzing the extracted micro sample, wherein a hole formed by being irradiated with an ion beam on the substrate is filled with a focused ion beam-induced gas-assisted deposition layer, and the gas-assisted deposition layer is covered with a laser beam induced gas-assisted deposition layer.

(21) An instrument for fabrication and observation by ion beam includes: an ion gun; an optical system for converging and deflecting an ion beam emitted from the ion gun; means for irradiating a sample with the ion beam so as to be processed; a detector for detecting secondary particles emitted from the sample irradiated with the ion beam; means for forming an image by the detected secondary particles; and means for irradiating and scanning a hole formed in the surface of the sample to form an ion beam gas assisted deposition layer in the hole, wherein the ion beam gas assisted deposition film is formed by controlling the ion beam so as to fall on a part of a side wall of the hole and so as not to fall on another part in an area scanned with the ion beam.

(22) An electronic device manufacturing method includes: a step of, after an arbitrary process in a manufacturing process of processing a sample and forming an electronic device, irradiating the sample with an ion beam to process a part of the surface of the sample for inspecting the sample; and a step of forming the ion beam gas assisted deposition film in a hole formed in the sample surface by the process while setting an area scanned with the ion beam to be almost the same as the opening area of the hole in the sample surface and controlling the area scanned with the ion beam so as to be moved with respect to the position of the hole, wherein the sample is inspected and, after that, the sample is put back into a process next to the arbitrary process and the manufacturing process is continued.

According to the invention, a technique is realized for filling, at high speed, a hole from which a sample has been extracted with an FIB, including a novel inspecting and analyzing method, an electronic device manufacturing method, and an instrument for fabrication and observation, in which a substrate is not discarded for evaluation uselessly and, even when a wafer from which a sample for inspection has been extracted is put back into the process, a defect is not caused.

What is claimed is:

1. A sample processing method comprising:
    a step of forming a sample piece to be analyzed by an analyzer, by irradiating an ion beam to a position of a sample where said sample piece and the sample are separated, and by etching the position by irradiating with the ion beam;
    a step of removing the sample piece from the sample, whereby a hole is formed in a position where the sample piece was removed from the sample, the hole having an opening area pattern; and
    a step of filling the hole formed in the sample using a focused ion beam, whereby the hole is buried with a deposition layer formed using the focused ion beam until a whole region of the deposition layer reaches a surface of the sample,
    wherein, in the step of filling the hole, the focused ion beam is scanned in a first scanning area pattern within the open area pattern and being smaller than the opening area pattern of the hole and overlapping a part of walls of the hole, to which the focused ion beam is scanned, inside the hole with a supply of a deposition gas, whereby a part of the deposition layer grows so as to reach the surface of the sample in a first differential area pattern within the open area pattern and representing a differential between the opening area pattern and the first scanning area pattern, and
    wherein the focused ion beam is scanned in a second scanning area pattern within the first scanning area pattern and having a shape of a shrunk area pattern of the first scanning area pattern, being on top of a part of the first scanning area pattern, and overlapping a portion of the same part of walls of the hole being scanned under the first scanning pattern, to which the focused ion beam is scanned, inside the hole with supply of the deposition gas after said focused ion beam is scanned in the first scanning area, whereby a part of the deposition layer grows so as to reach the surface of the sample in a second differential area pattern within the first scanning area pattern and representing a differential between the first scanning area pattern and the second scanning area pattern.

2. The sample processing method according to claim 1, wherein an ion beam current of the focused ion beam is set to 1 nA or higher.

3. The sample processing method, according to claim 1, further comprising:
    a step of covering the deposition layer with a protection film by applying a liquid material such that the deposition layer has no surface that is exposed after the step of filling the hole with the deposition layer.

4. The sample processing method, according to claim 1, wherein the first scanning area pattern and the second scanning area pattern are within a bottom area of the hole.

5. The sample processing method, according to claim 1, wherein after the focused ion beam is scanned in the second scanning area pattern, the focused ion beam is scanned in a third scanning area pattern within the second scanning area pattern and having a shrunk area pattern of the second scanning area pattern, being on top of a part of the second scanning area pattern, and overlapping a portion of the same part of walls of the hole being scanned under the second scanning pattern, to which the focused ion beam is scanned, inside the hole with the supply of the deposition gas, whereby a part of the deposition layer reaches the surface of the sample in a third differential area pattern within the second scanning area pattern and representing a differential between the second scanning area and the third scanning area pattern.

6. The sample processing method of claim 1, wherein the first differential area pattern is not scanned by the focused ion beam during scanning of the first scanning area pattern.

7. A sample processing method comprising:
a step of forming a sample piece to be analyzed by an analyzer, by irradiating an ion beam to a position of a sample where the sample piece and the sample are separated, and by etching the position by irradiating with the ion beam;
a step of removing the sample piece from the sample, whereby a hole is formed in a position where there was the sample piece was removed from the sample, the hole having an opening area pattern; and
a step of filling the hole formed in the sample using a focused ion beam, whereby the hole is buried with a deposition layer formed using the focused ion beam until a whole region of the deposition layer reaches a surface of the sample,
wherein, there are scanning area patterns within the opening area pattern and being on top of a part of walls of the hole and having progressively smaller sizes, to which the focused ion beams are scanned inside the hole with a supply of a deposition gas, each subsequent scanning area pattern being within a previous scanning area pattern and overlapping a portion of the same part of walls of the hole being scanned under the previous scanning area pattern, and
wherein, in the step of filling the hole, the focused ion beam scans to the scanning area patterns from a larger size in an order of decreasing size, whereby a part of the deposition layer reaches the surface of the sample in a differential area pattern within the open area pattern and representing a differential between one scanning area pattern and a immediately preceeding scanning area pattern prior to scanning by the focused ion beam, and a growth of the deposition layer is conducted until the whole region of the deposition layer reaches the surface of the sample.

8. The sample processing method of claim 7, wherein the differential area pattern for each of the one scanning area pattern is not scanned by the focused ion beam during scanning of each of the one scanning area pattern.

9. A sample processing method comprising:
a step of forming a sample piece to be analyzed by an analyzer, by irradiating an ion beam to a position of a sample where said sample piece and the sample are separated, and by etching the position by irradiating with the ion beam;
a step of removing the sample piece from the sample, whereby a hole is formed in a position where there was the sample piece was removed from the sample, the hole having an opening area pattern; and
a step of filling the hole formed in the sample using a focused ion beam, whereby the hole is buried with a deposition layer formed using the focused ion beam until a whole region of the deposition layer reaches a surface of the sample,
wherein, in the step of filling the hole, the focused ion beam is scanned in a first scanning area pattern within the open area pattern and being smaller than an opening area pattern of the hole and overlapping a part of walls of the hole, to which the focused ion beam is scanned, inside the hole with a supply of a deposition gas, whereby a part of the deposition layer grows so as to reach the surface of the sample in a first differential area pattern within the open area pattern and representing a differential between the opening area pattern and the first scanning area pattern, wherein the first differential area pattern is not scanned by the focused ion beam, and
wherein the focused ion beam is scanned in a second scanning area pattern within the first scanning area pattern and having a shape of a shrunk area pattern of the first scanning area pattern, being on top of a part of the first scanning area pattern, and overlapping a portion of the same part of walls of the hole being scanned under the first scanning area pattern, to which the focused ion beam is scanned, inside the hole with supply of the deposition gas after said focused ion beam is scanned in the first scanning area.

10. The sample processing method according to claim 9, wherein after the focused ion beam is scanned in the second scanning area pattern, the focused ion beam is scanned in a third scanning area pattern within the second scanning pattern area and having a shrunk area pattern of the second scanning area pattern, being on top of a part of the second scanning area pattern, and overlapping a portion of the same part of walls of the hole being scanned under the second scanning area pattern, to which the focused ion beam is scanned, inside the hole with the supply of the deposition gas.

11. The sample processing method according to claim 10, wherein a part of the deposition layer grows so as to reach the surface of the sample in a second differential area pattern within the first scanning area pattern and representing a differential between the first scanning area pattern and the second scanning area pattern.

12. The sample processing method according to claim 10, wherein a part of the deposition layer reaches the surface of the sample in a third differential area pattern within the second scanning area pattern and representing a differential between the second scanning area pattern and the third scanning area pattern.

13. The sample processing method according to claim 9, further comprising:
a step of covering the deposition layer with a protection film by applying a liquid material such that the deposition layer has no surface that is exposed after the step of filling the hole with the deposition layer.

* * * * *